United States Patent
Simmonds et al.

(12)

(10) Patent No.: US 6,605,611 B2
(45) Date of Patent: Aug. 12, 2003

(54) BASE ANALOGUES

(75) Inventors: Adrian Christopher Simmonds, Amersham (GB); Alan Hamilton, Amersham (GB); Clifford Smith, Tring (GB); David Loakes, Letchworth (GB); Daniel Brown, Cambridge (GB); Fergal Hill, Cambridge (GB); Shiv Kumar, Belle Mead, NJ (US); Satyam Nampalli, Belle Mead, NJ (US); Mark McDougall, Bethlehem, PA (US)

(73) Assignee: Nycomed Amersham PLC, Little Chalfont (GB)

( * ) Notice: Subject to any disclaimer, the term of this patent is extended or adjusted under 35 U.S.C. 154(b) by 0 days.

(21) Appl. No.: 10/233,993

(22) Filed: Sep. 3, 2002

(65) Prior Publication Data

US 2003/0060431 A1 Mar. 27, 2003

Related U.S. Application Data

(62) Division of application No. 09/463,501, filed as application No. PCT/GB98/02306 on Jul. 31, 1998, now Pat. No. 6,444,682.

(30) Foreign Application Priority Data

Jul. 31, 1997 (GB) .............................................. 9716231

(51) Int. Cl.[7] .................... A61K 31/495; A61K 31/519; C07D 487/00; C07D 403/02; C07D 471/02
(52) U.S. Cl. .................... 514/274; 514/248; 514/262.1; 514/264.1; 514/269; 514/461; 514/23; 544/236; 544/256; 544/279; 544/298; 544/315; 546/118; 546/121; 546/123; 536/22.1
(58) Field of Search ................................. 514/274, 248, 514/262.1, 264.1, 209, 461, 23; 544/236, 256, 279, 298, 315; 546/118, 121, 123; 536/22.1

(56) References Cited

U.S. PATENT DOCUMENTS

| | | | | |
|---|---|---|---|---|
| 4,965,350 A | * | 10/1990 | Inoue et al. | .................... 536/28 |
| 5,948,648 A | | 9/1999 | Khan et al. | .................... 435/87 |
| 6,239,159 B1 | | 5/2001 | Brown et al. | ................ 514/394 |
| 6,287,821 B1 | | 9/2001 | Shi et al. | .................... 435/91.2 |
| 6,320,035 B1 | | 11/2001 | Muhlegger et al. | ......... 536/23.1 |

FOREIGN PATENT DOCUMENTS

| | | |
|---|---|---|
| EP | 0 235 301 | 9/1987 |
| JP | 62255499 | 11/1987 |
| WO | WO 93/05175 | 3/1993 |
| WO | WO 96/34867 | 11/1996 |
| WO | WO 97/28177 | 8/1997 |
| WO | WO 98/49177 | 11/1998 |

OTHER PUBLICATIONS

Abdullah et al., "Fluorescence Studies of Selected 5–X Thiazolo[5,4–d] Pyrimidines," *ACGC Chemical Research Communications* 4:23–25 (1996).

Ahmed, "Synthesis of Some 4,5–Cyclo Cytosine Nucleosides," *Bulletin of the Polish Academy of Sciences Chemistry* 44(4):209–213 (1996).

Dinan et al., "Simplified Synthesis of 5–Mercaptouracil Riboside Derivatives," *J. Org. Chem.* 47:1769–1772 (1982).

Griengl et al., "5–(haloalkyl)–2'deoxyuridines: A Novel Type of Potent Antiviral Nucleoside Analogue," *J. Med. Chem.* 28(11):1679–1684 (1985).

Griengl et al., "5–2'deoxy . . . a novel . . . antiviral . . . analog," *J. Med. Chem.* 28(11):1679–1684 (1985).

Loakes et al., "Synthesis of Bicyclic N[4]–Oxycytidine Derivatives," *Nucleosides & Nucleotides* 13(1–3);679–706 (1994).

Loakes et al., "The Synthesis of Bicyclic N[4]–Amino–2'–Deoxyxytidine Derivatives," *Nucleosides & Nucleotides* 14:(3–5), 291–293 (1995).

Meunier et al., "Synthèse, caractérisation et propiétés cytoxiques des premiers métallocénocucléosides," *Eur. J. Med. Chem* 26(3):351–362 (1991).

Nara et al., "Nucleosides and Nucleotides. 135. DNA Duplex and Triplex Formation and Resistance to Nucleolytic Degradation of Oligodeoxynucleotides Containing syn–Norspermidine at the 5–position of 2'–Deoxyuridine," *Bioconjugate Chem.* 6(1):54–61 (1995).

* cited by examiner

Primary Examiner—Richard L. Raymond
Assistant Examiner—Sudhaker B. Patel
(74) Attorney, Agent, or Firm—Marshall, Gerstein & Borun

(57) ABSTRACT

Nucleoside analogues or base analogues having structure (I), where X=O or NH or S, Y=N or CHR[6] or CR[6], W=N or NR[6] or CHR[6] or CR[6] or S, n=1 or 2; each R[6] is independently H or O or alkyl or alkenyl or alkoxy or aryl or a reporter moiety; where necessary (i.e. when Y and/or W is N or CR[6] where R[6] is not O) a double bond is present between Y and W or W and W, and Q is H or a sugar or a sugar analogue or a nucleic acid backbone or backbone analogue.

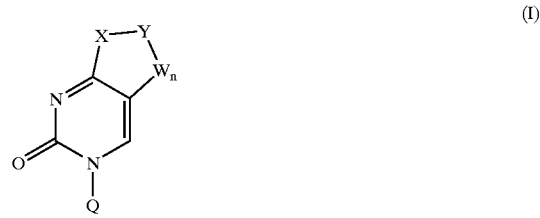

(I)

16 Claims, No Drawings

BASE ANALOGUES

This application is a divisional of U.S. Ser. No. 09/463,501, filed Apr. 18, 2000, which issued on Sep. 3, 2002 as U.S. Pat. No. 6,444,682, and which is a 371 of PCT/GB98/02306 filed Jul. 31, 1998, which claims priority to GB 9716231.7, filed Jul. 31, 1997.

This invention concerns base analogues which may be used to make nucleoside analogues and nucleotide analogues which may be incorporated into nucleic acids and nucleic acid analogues e.g. PNA. Some of these analogues are base-specific and may be incorporated into DNA or RNA or PNA in the place of a single native base i.e. A, T, G, or C. Other analogues have the potential for base-pairing with more than one native base or base analogue.

The present invention provides a compound having the structure

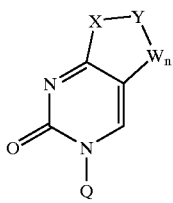

where

X=O or NH or S

Y=N or $CHR^6$ or $CR^6$ or CO

W=N or $NR^6$ or $CHR^6$ or $CR^6$ or S or CO n=1 or 2 or 3 each $R^6$ is independently H or alkyl or alkenyl or alkoxy or aryl or a reporter moiety, where necessary (i.e. when Y and/or W is N or $CR^6$) a double bond is present between Y and W or W and W, and Q is H or a sugar or a sugar analogue, provided that
i) when n is 2 and X is NH and W is $CHR^6$ or $CR^6$, and Y is CO, then at least one reporter moiety is present,
ii) when n is 1 and X is NH and W is N or $NR^6$, then at least one reporter moiety is present,
iii) when n is 1 and X is O and Y is $CHR^6$ or $CR^6$ and W is $CHR^6$ or $CR^6$, then at least one $R^6$ is a reporter moiety which is a reactive group or signal moiety or solid surface joined to the remainder of the molecule by a linker of at least 3 chain atoms,
iv) when n is 1 and X is NH and Y is $CHR^6$ or $CR^6$ and W is $CHR^6$ or $CR^6$, then a least one reporter moiety is present,
v) when W is S, then n is 2 and $W_n$ is —$CHR^6$—S— or =$CR^6$—S—,
vi) when n is 2 and X is NH and Y is $CHR^6$ or $CR^6$, then at least one $R^6$ is a reporter moiety which is a reactive group or signal moiety or solid surface joined to the remainder of the molecule by a linker of at least 3 chain atoms.

Q may be

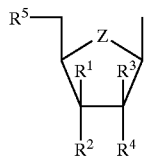

where

Z is O, S, Se, SO, $NR^9$ or $CH_2$, $R^1$, $R^2$, $R^3$ and $R^4$ are the same or different and each is H, OH, F, $NH_2$, $N_3$, O-hydrocarbyl or a reporter moiety, $R^5$ is OH, SH or $NH_2$ or mono-, di- or tri-phosphate or -thiophosphate, or corresponding boranophosphate, or one of $R^2$ and $R^5$ is a phosphoramidite or other group for incorporation in a polynucleotide chain, or a reporter moiety, or Q consists of one of the following modified sugar structures Acyclic Sugars

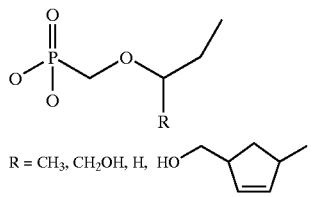

$R = CH_3, CH_2OH, H,$

Morpholino Backbone

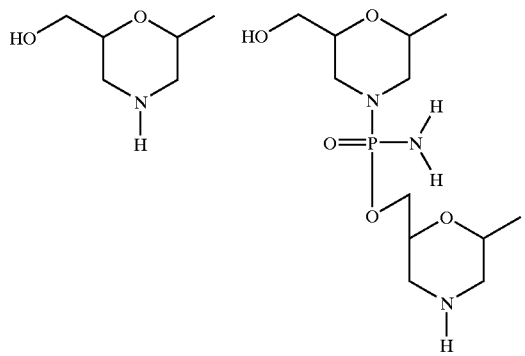

or Q is a nucleic acid backbone consisting of sugar-phosphate repeats or modified sugar-phosphate repeats (e.g. LNA) (Koshkin et al, 1998, Tetrahedron 54, 3607–30) or a backbone analogue such as peptide or polyamide nucleic acid (PNA). (Nielsen et al, 1991, Science 254, 1497–1500).

When Q is H, these compounds are base analogues. When Q is a sugar or sugar analogue or a modified sugar, these compounds are nucleotide analogues or nucleoside analogues. When Q is a nucleic acid backbone or a backbone analogue, these compounds are herein called nucleic acids or polynucleotides.

Preferred general structures covered by the invention are

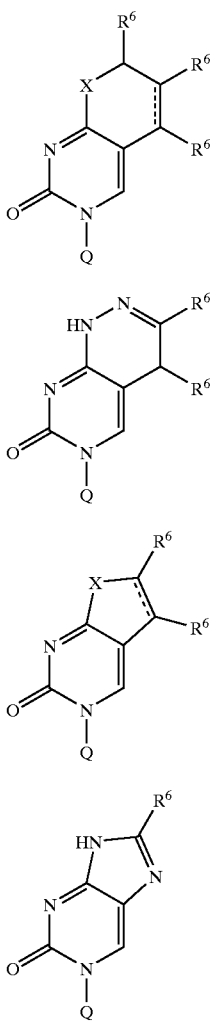

(1)
(2)
(3)
(4)

In the context of this invention, a nucleotide is a naturally occurring compound comprising a heterocyclic base and a backbone including a phosphate. A nucleoside is a corresponding compound in which a backbone phosphate may or may not be present. Nucleotide analogues and nucleoside analogues are analogous compounds having different bases and/or different backbones. A nucleoside analogue is a compound which is capable of forming part of a nucleic acid (DNA or RNA or PNA) chain, and is there capable of base-pairing with a base in a complementary chain or base stacking in the appropriate nucleic acid chain. A nucleoside analogue may be specific, by pairing with only one complementary nucleotide; or degenerate, by base pairing with more than one of the natural bases, e.g. with pyrimidines (T/C) or purines (A/G); or universal, by pairing with each of the natural bases with little discrimination; or it may pair with another analogue or itself.

In one preferred aspect of the invention, the base analogue is linked to a sugar moiety such as ribose or deoxyribose to form a nucleoside analogue. When the group $R^5$ is triphosphate, the nucleoside triphosphate analogues of the invention are capable of being incorporated by enzymatic means into nucleic acid chains.

Preferably n is 1 or 2, and W is N or $NR^6$ or $CR^6$ or $CHR^6$.

In another preferred aspect, the nucleoside analogue or nucleotide analogue which contains a base analogue as defined is labelled with at least one reporter moiety. A reporter moiety may be any one of various things. It may be a radioisotope by means of which the nucleoside analogue is rendered easily detectable, for example 32-P or 33-P or 35-S incorporated in a phosphate or thiophosphate or phosphoramidite or H-phosphonate group, or alternatively 3-H or 14-C or an iodine isotope. It may be an isotope detectable by mass spectrometry or NMR. It may be a signal moiety e.g. an enzyme, hapten, fluorophore, chromophore, chemiluminescent group, Raman label or electrochemical label. The reporter moiety may comprise a signal moiety and a linker group joining it to the remainder of the molecule, which linker group may be a chain of up to 30 carbon, nitrogen, oxygen and sulphur atoms, rigid or flexible, unsaturated or saturated as well known in the field. The reporter moiety may comprise a solid surface and a linker group joining it to the rest of the molecule. Linkage to a solid surface enables the use of nucleic acid fragments containing nucleoside analogues to be used in assays including bead based probe assays or assays involving arrays of nucleic acid samples or oligonucleotides which are interrogated with e.g. oligonucleotide or nucleic acid or even peptide or protein probes. The reporter moiety may consist of a linker group with a terminal or other reactive group, e.g. $NH_2$, OH, COOH, $CONH_2$ or SH, by which a signal moiety and/or solid surface may be attached, before or after incorporation of the nucleoside analogue in a nucleic acid chain.

To avoid risk of steric hindrance, a linker preferably has at least three chain atoms, e.g. —$(CH_2)_n$— where n is at least 3.

Two (or more) reporter moieties may be present, e.g. a signal moiety and a solid surface, or a hapten and a different signal moiety, or two fluorescent signal groups to act as donor and acceptor. Various formats of these arrangements may be useful for separation or detection purposes.

Purine and pyrimidine nucleoside derivatives labelled with reporter moieties are well known and well described in the literature. Labelled nucleoside derivatives have the advantage of being readily detectable during sequencing or other molecular biology techniques.

$R^1$, $R^2$, $R^3$ and $R^4$ may each be H, OH, F, $NH_2$, $N_3$, O-alkyl or a reporter moiety. Thus ribonucleosides, and deoxyribonucleosides and dideoxyribonucleosides are envisaged together with other nucleoside analogues. These sugar substituents may contain a reporter moiety in addition to any that Might be present on the base.

$R^5$ is OH, SH, $NH_2$ or mono-, di- or tri-phosphate or -thiophosphate or corresponding boranophosphate. Alternatively, one of $R^2$ and $R^5$ may be a phosphoramidite or H-phosphonate or methylphosphonate or phosphorothioate or amide, or an appropriate linkage to a solid surface e.g. hemisuccinate controlled pore glass, or other group for incorporation, generally by chemical means, in a polynucleotide chain. The use of phosphoramidites and related derivatives in synthesising oligonucleotides is well known and described in the literature.

In the new base or nucleoside analogues to which this invention is directed, at least one reporter moiety is preferably present in the base analogue or in the sugar moiety or a phosphate group. Reporter moieties may be introduced into the sugar moiety of a nucleoside analogue by literature methods (e.g. J. Chem. Soc. Chem. Commun. 1990, 1547–8; J. Med. Chem., 1988, 31. 2040–8). Reporters in the form of isotopic labels may be introduced into phosphate groups by literature methods (Analytical Biochemistry, 214, 338–340, 1993; WO 95/15395).

Nucleoside analogues of this invention are useful for labelling DNA or RNA or for incorporating in oligonucleotides or PNA. A reporter moiety is attached at a position where it does not have a significant detrimental effect on the physical or biochemical properties of the nucleoside analogue, in particular its ability to be incorporated in single stranded or double stranded nucleic acid.

A template containing the incorporated nucleoside analogue of this invention may be suitable for copying in nucleic acid synthesis. If a reporter moiety of the incorporated nucleoside analogue consists of a linker group, then a signal moiety can be introduced into the incorporated nucleoside analogue by being attached through a terminal or other reactive group of the linker group.

A nucleoside analogue triphosphate of this invention may be incorporated by enzymes such as terminal transferase to extend the 3' end of nucleic acid chains in a non-template directed manner. Tails of the nucleoside analogue triphosphate produced in this way may be detected directly in the absence of any reporter label by use of antibodies directed against the nucleoside analogue. The analogues when incorporated into oligonucleotides or nucleic acids may be acted upon by nucleic acid modification enzymes such as ligases or restriction endonucleases.

In primer walking sequencing, a primer/template complex is extended with a polymerase and chain terminated to generate a nested set of fragments where the sequence is read after electrophoresis and detection (radioactive or fluorescent) or directly in a mass spectrometer A second primer is then synthesised using the sequence information near to the end of the sequence obtained from the first primer. This second ("walking") primer is then used for sequencing the same template. Primer walking sequencing is more efficient in terms of generating less redundant sequence information than the alternative "shot gun" approach.

The main disadvantage with primer walking is the need to synthesise a primer after each round of sequencing. Cycle sequencing requires primers that have annealing temperatures near to the optimal temperature for the polymerase used for the cycle sequencing. Primers between 18 and 24 residues long are generally used for cycle sequencing. The size of a presynthesised walking primer set required has made primer walking cycle sequencing an impractical proposition. The use of base analogues that are degenerate or universal addresses this problem. The use of such analogues that are also labelled, e.g. the nucleoside analogues of this invention will also help to overcome the problem. Preferred reporters for this purpose are radioactive isotopes or fluorescent groups, such as are used in conventional cycle sequencing reactions. Where the nucleoside analogues are base specific chain terminators they may be used in chain terminating sequencing protocols.

The final analysis step in DNA sequencing involves the use of a denaturing polyacrylamide electrophoresis gel to separate the DNA molecules by size. Electrophoretic separation based solely on size requires the complete elimination of secondary structure from the DNA. For most DNA this is typically accomplished by using high concentrations of urea in the polyacrylamide matrix and running the gels at elevated temperatures. However certain sequences, for example those capable of forming "stem loop" structures retain secondary structure and, as a result, display compression artefacts under standard electrophoresis conditions. Here, adjacent bands of the sequence run at nearly the same position on the gel, "compressed" tightly together. Such loops are typically formed when a number of GC pairs are able to interact since GC pairs can form 3 hydrogen bonds compared to the 2 hydrogen bonds of AT pairs.

A second form of compression artefact is seen when rhodamine-labelled terminators are used and there is a G residue close to the terminus. In these cases, anomalous mobility of the DNA strand in a gel is often seen, possibly due to an interaction between the dye and the G residue.

Thus, compression artefacts appear to be caused whenever stable secondary structures exist in the DNA under the conditions prevailing in the gel matrix during electrophoresis. The folded structure runs faster through the gel matrix than an equivalent unfolded DNA.

Currently, gel compression artefacts are eliminated in one of two ways. One is to change to a stronger denaturing condition for the gel, for example 40% formamide with 7 M urea. The other method is to incorporate a derivative of dGTP during the synthesis of DNA. An alternative method would involve the use of a dCTP analogue which reduced the hydrogen bonding potential of the G-C base pair. The nucleoside analogues of this invention may be useful in this regard.

The nucleoside analogues of this invention can also be used in any of the existing applications which use native nucleic acid probes labelled with haptens, fluorophores or other reporter groups, for example on Southern blots, dot blots and in polyacrylamide or agarose gel based methods or solution hybridization assays and other assays in microtitre plates or tubes or assays of oligonucleotides or nucleic acids such as on microchips. The probes may be detected with antibodies targeted either against haptens which are attached to the base analogues or against the base analogues themselves which would be advantageous in avoiding additional chemical modification. Antibodies used in this way are normally labelled with a detectable group such as a fluorophore or an enzyme. Fluorescent detection may also be used if the base analogue itself is fluorescent or if there is a fluorophore attached to the nucleoside analogue.

The use of the different mass of the nucleoside analogue may also be used as a means of detection as well as by the addition of a specific mass tag identifyer to it. Methods for the analysis and detection of specific oligonucleotides, nucleic acid fragments and oligonucleotide primer extension projects based on mass spectrometry have been reported. (Beavis R. C., Chait B. T., U.S. Pat. No. 5,288,644, Wu K. J. et al. Rapid Commun. Mass Spectrom. 7,142 (1993), Koster H. WO 94/16101.

These methods are usually based on matrix assisted laser ionisation and desorption, time of flight (MALDITOF) mass spectrometry. They measure the total mass of an oligonucleotide or fragment and from this the sequence of the specific oligonucleotide may be able to be ascertained. In some cases the mass of the oligonucleotide or fragment may not be unique for a specific sequence. This will occur when the ratio of the four natural bases, ACGT, is similar in different sequences.

For example, a simple 4 mer oligonucleotide, ACGT will have the same mass as 24 other possible mers, for example; CAGT, CATG, CGTA, CTAG, CTGA etc.

With longer nucleic acid fragments it may be difficult to resolve the differences in mass between 2 fragments because of a lack of resolution in the spectrum at higher molecular weights. The incorporation of the analogues described here can be used to help identify the specific oligonucleotide or nucleic acid fragment as their masses are different from those of the natural bases.

For example, the two sequences ACGT and CAGT can be identified in the presence of one another by mass spectrometry if, for example one of the natural nucleotides in one of the sequences is replaced with one of the analogues described in this invention. For example, in the oligonucleotide CAGT the T can be replaced by an analogue with little effect on a specific application, for example hybridisation or enzymatic incorporation. Yet the two sequences can be readily identified in the mass spectrometer because of the change in mass due to the introduction of the analogue base.

Not only can mass modifications be made to the bases or linkers but also to the sugars or inter nucleotide linkages. For example thio sugars or phosphorothioate linkages will also result in distinctive mass changes.

A mixture of modifications at the base, linker, nucleoside or nucleotide either separately or together can give rise to a number of molecules with different masses which will be useful to define a specific sequence accurately by its mass, especially in multiplex nucleic acid hybridisation or sequencing applications.

The nucleoside analogues of the present invention with the combination of molecular diversity and increased numbers of positions where reporter groups may be added can result in a series of improved enzyme substrates.

Another preferred aspect of the invention is to incorporate the nucleoside analogue triphosphate into DNA by means of a polymerase but without a reporter label for the purpose of random mutagenesis. It has been shown by Zaccolo et al, 1996, J. Mol. Biol. 255, 589–603 that when nucleotide analogues with ambivalent base pairing potential are incorporated by the PCR into DNA products, they induce the formation of random mutations within the DNA products. In the above publication, the nucleotide analogue dPTP was shown to be incorporated into DNA by Taq polymerase in place of TTP and, with lower efficiency, dCTP. After 30 cycles of DNA amplification, the four transition mutations A→G, T→C, G→A and C→T were produced. The compound 8-oxodGTP was also used to cause the formation of the transversion mutations A→C and T→G. The nucleoside analogue triphosphates with ambivalent base pairing potential described within this invention may be used for a similar purpose.

RNA is an extremely versatile biological molecule. Experimental studies by several laboratories have shown that in vitro selection techniques can be employed to isolate short RNA molecules from RNA libraries that bind with high affinity and specificity to proteins, not normally associated with RNA binding, including a few antibodies, (Gold, Allen, Binkley, et al,1993, 497–510 in The RNA World, Cold Spring Harbor Press, Cold Spring Harbor N.Y., Gold, Polisky, Unlenbeck, and Yarus, 1995, Annu. Rev. Biochem. 64: 763–795, Tuerk and Gold, 1990, Science 249:505–510, Joyce, 1989, Gene 82:83–87, Szostak, 1992, Trends Biochem. Sci 17:89–93, Tsai, Kenan and Keene, 1992, PNAS 89:8864–8868, Tsai, Kenan and Keene, 1992, PNAS 89:8864–8868, Doudna, Cech and Sullenger, 1995, PNAS 92:2355–2359). Some of these RNA molecules have been proposed as drug candidates for the treatment of diseases like myasthenia gravis and several other auto-immune diseases.

The basic principle involves adding an RNA library to the protein or molecule of interest. Washing to remove unbound RNA. Then specifically eluting the RNA bound to the protein or other molecule of interest. This eluted RNA is then reverse transcribed and amplified by PCR. The DNA is then transcribed using modified nucleotides (either 2' modifications to give nuclease resistance e.g. 2' F, 2' $NH_2$, 2' $OCH_3$ and/or C5 modified pyrimidines and/or C8 modified purines). Those molecules that are found to bind the protein or other molecule of interest are cloned and sequenced to look for common ("consensus") sequences. This sequence is optimised to produce a short oligonucleotide which shows improved specific binding which may then be used as a therapeutic.

The base analogues described here, when converted to the deoxy- or ribonucleoside triphosphate or deoxy- or ribonucleoside phosphoramidite, will significantly increase the molecular diversity available for this selection process. This may lead to oligonucleotides with increased binding affinity to the target that is not available using the current building blocks.

The secondary structure of nucleic acids is also important when considering ribozyme function. The base analogues of the present invention may cause the formation of secondary structures which would otherwise be unavailable using native bases or other modified nucleotide derivatives.

The hybridization binding properties of nucleic acids incorporating base analogues of the present invention may have particular application in the antisense or antigene field.

The base analogues of the present invention may have properties which are different to those of the native bases and therefore are particularly suited to other important applications. In particular, the interaction of these base analogues with enzymes may be extremely important in vivo and may result in the development of new anti-viral therapeutics or therapeutics for non-viral diseases.

A wide range of nucleoside and nucleotide analogues have been developed to form an original class of antiviral agents. Some of these compounds have already been approved by the US FDA for use in the treatment of viral diseases. Examples are compounds like 3'-deoxy-3'-azidothymidine (AZT, Zidovudine) and 2',3'-dideoxy-3'-thiacytidine (3TC, Lamivudine) for the treatment of HIV infections. Other compounds like (S)-1-(3-hydroxy-2-phosphonylmethoxypropyl)cytosine (HPMPC, cidofovir), 9-(2-phosphonyl-methoxyethyl)adenine (PMEA, adefovir) and (R)-9-(2-phosphonylmethoxypropyl)adenine (PMPA), the acyclic nucleoside phosphonate analogues, are in clinical trials. These compounds either act as absolute DNA chain terminators or result in termination after incorporation of consecutive molecules causing inhibition of the viral DNA polymerase. It should be noted that some of these compounds are the unnatural β-L enantiomers which show significantly decreased interaction with the host DNA polymerases compared to the viral polymerases.

One of the problems in the treatment of viral infections with nucleoside and nucleotide drugs is the ability of the virus to develop resistance by a series of mutations to the viral reverse transcriptase gene that are selected as a result of drug pressure. Therefore, it is often necessary to use combination drug therapies to overcome this problem. However, the number of suitable, available compounds for therapy is limited. The subject of this invention could be useful in expanding the range of nucleoside and nucleotide antiviral drugs.

Those skilled in the art of organic chemistry will recognise that there is a variety of approaches that can be taken to the compounds claimed within the scope of the claims. In addition to those approaches detailed in the experimental section those illustrated below are possible.

Scheme 1

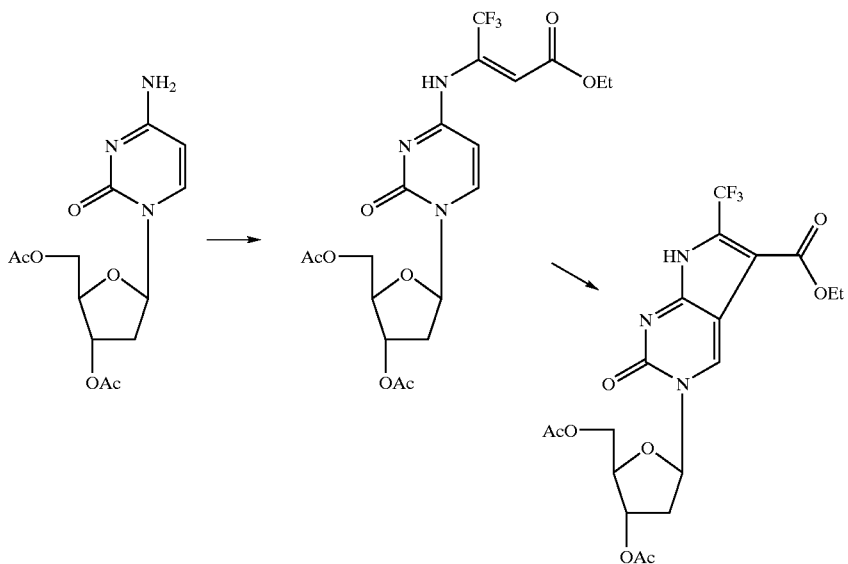

In order to synthesise a compound where W=CR$_6$ and R$_6$ contains a reporter group the reaction sequence in scheme 1 can be used.

Diacetyl protected deoxycytidine an be treated with ethyltrifluorobutynoate to get an enamine intermediate. The enamine is expected to undergo oxidative cyclization under Pd(OAc)$_2$/DMA/70° C. reaction conditions (Fukuda et al, Bioorganic & Medicinal Chemistry Letters, 1997, 7, 1683). The ester group thus incorporated can be exploited to conjugate with a fluorescent dye, e.g. after converting to a suitable functional group such as an active ester it can be either reacted directly with an amine containing fluorescent dye or with a with a suitably protected diamine to extend the linker group prior to signal attachment.

When X and W both equal N the following approach in scheme 2 can be undertaken

Scheme 2

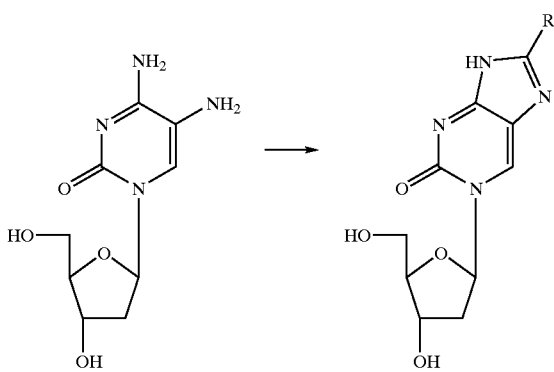

Treatment of the known 5-aminocytidine (Kalman and Goldman, BBRC, 1981, 102, 682) with ethylformate leads to the product (R=H).

For the 8-oxoG analogue (i.e. R=O) treatment of the initial diamine with a variety of reagents (COCl$_2$, carbonyl diimidazole, diphenyl carbonate) leads to the desired product.

These can be converted to its 5'-triphosphate using methods outlined in the experimental section and its 5'-dimethoxytrityl-3'-phosphoramidite by standard literature methods.

The introduction of a linker (R$_6$) to the 8-position (conventional purine numbering) can be carried out using the reactivity of this position to bromination followed by alkylation with, for example, hexane diamine.

Experimental Schemes

General Procedure

Ion exchange (IE) HPLC was performed on a Waters analytical system running under Millenium Chromatography Manager software. For analytical IE analysis a Amersham Pharmacia Biotech □RPC ST (C$_2$/C$_{18}$) reverse phase column (4.6×100 mm) was used, with (method A) a gradient of 0–25% buffer B over 30 min at a flow rate of 1 mL/min or (method B) a gradient of 0–50% buffer B over 30 min and the same flow rate as method A. Buffer A was 0.1 M TEAB and buffer B was 100% acetonitrile TLC analysis was performed on 0.2 mm-thick precoated Merck silica gel 60 F$_{254}$ plates. Flash silica gel chromatography was performed with 230–400 mesh 60-Å silica from Merck.

$^1$H NMR spectra (300 MHz) were recorded on a Varian Gemini system

EXAMPLE 1

Synthesis of 1-(2'-deoxy-5'-triphospho-β-D-ribofuranosyl)piperidino[2,3-d]pyrimidine-2(1H)-one (1.6)

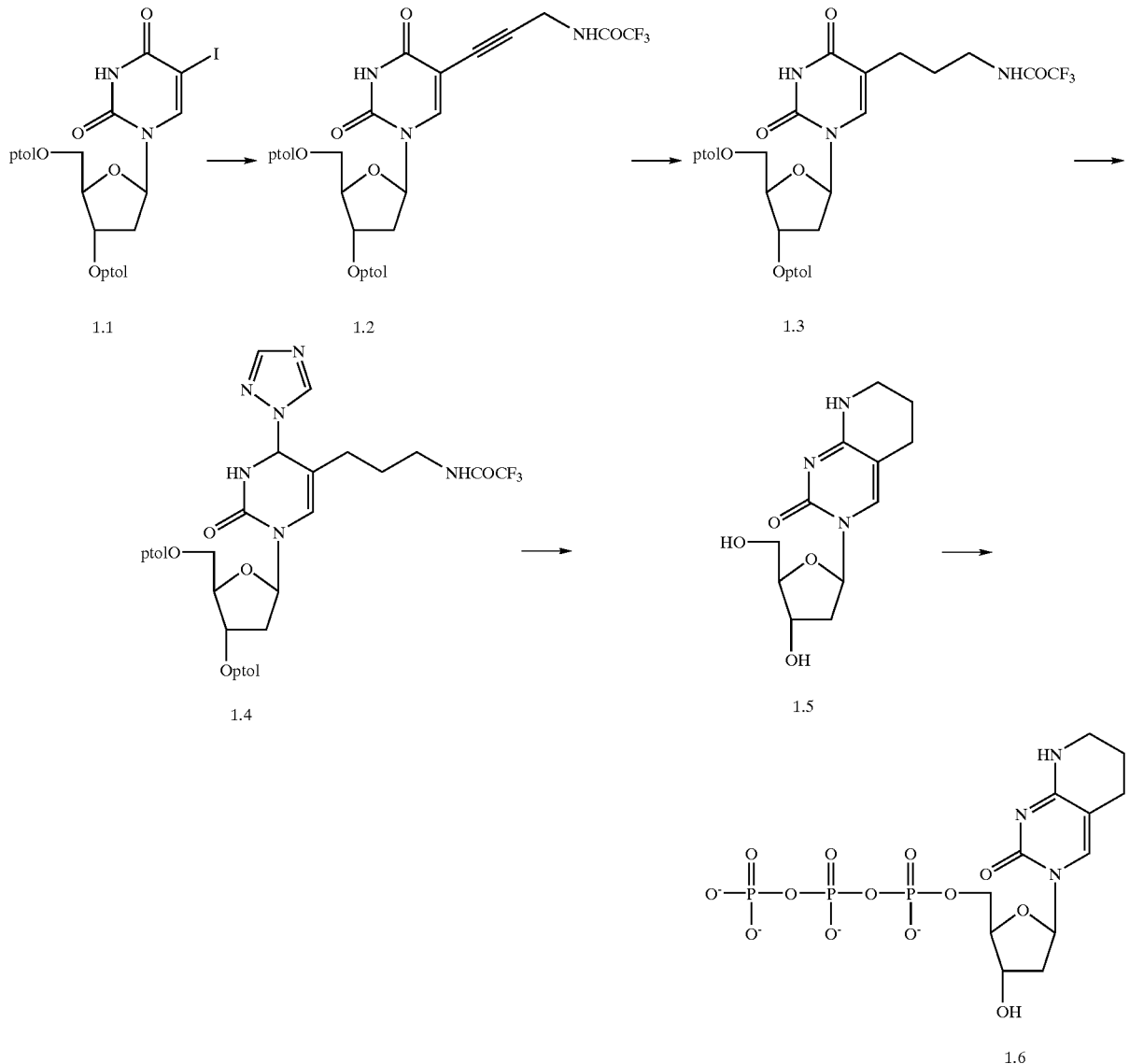

3',5'-Di-O-p-toluoyl-5-iodo-2'-deoxyuridine (1.1)

A stirred solution of 5-iodo-2'-deoxyuridine (2.45 g, 6.92 mmol) in anhydrous pyridine (50 mL) was cooled to 0° C. and p-toluoyl chloride (2.29, 17.3 mmol, 2.5 eq) was slowly added. The solution was allowed to warm to room temperature, heated at 50° C. for 3 hrs and then stirred at room temperature overnight. The solvent was evaporated in vacuo to give a white solid mass after repeated co-evaporation with EtOH. Chloroform was added and the organic phase was washed with 0.5 M $H_2SO_4$ (2×25 mL) then water (2×25 mL), dried over anhydrous sodium sulfate, filtered and evaporated to dryness. The crude material was crystallized at −18° C. in 100 mL of a mixture MeOH/CHCl₃ 5:1 to give 3.3 g of title compound (80% yield). m.p. 193° C. $^1H$ $d_6$-DMSO δ(ppm) 2.36 and 2.38 (6H, 2×s, 2×Me), 2.49–2.67 (2H, m, H2', H2"), 4.44–4.58 (3H, m, H4', H5', H5"), 4.50–4.55 (1H, m, H3'), 6.21 (1H, t, J=6.7 Hz, H1'), 7.30–7.36 (m, 4H, aromatic), 7.86–7.92 (m, 4H, aromatic), 8.08 (1H, s, H6), 11.79 (1H, brs, NH). m/z (MALDI-TOF MS) 613.6 (M+Na)+, 629.6 (M+K)+, $C_{25}H_{23}IN_2O_7$ requires 590.372.

3',5'-Di-O-p-toluoyl-5-N-trifluoroacetylaminopropargyl-2'-deoxyuridine (1.2)

In a three-necked flask containing 60 mL of freshly distilled DMF purged with nitrogen was added the nucleoside (1.1) (2.45 g, 4 mmol), N-propargyl trifluoroacetamide (1.81 g, 12 mmol, 3 eq), tetrakis-bis-triphenylphosphine-palladium(0) (115 mg, 0.1 mmol, 2.5% mmol), CuI (38 mg, 0.2 mmol, 5% mmol) and triethylamine (2.8 mL, 20 mmol, 5 eq). The reaction was purged with nitrogen and the solution stirred at room temperature overnight. After this time tetrakis-bis-triphenylphosphine-palladium(0) (115 mg, 0.1 mmol, 2.5% mmol), CuI (38 mg, 0.2 mmol, 5% mmol) were added and the stirring continued until TLC (EtOAc/Hexane 1:1) showed the reaction was complete (20 hrs). To the mixture solid EDTA disodium salt (0.5 g) was added, then the solvent was concentrated and diluted with 100 mL of chloroform. The solution was washed with 5% EDTA disodium salt (3×50 mL), water (2×50 mL) and brine (2×50 mL). The organic phase was dried over anhydrous sodium sulfate, filtered and evaporated to dryness. The crude brownish solid was purified by silica gel column chromatography (MeOH/CHCl$_3$ 0→2%) to give 2.2 g of pure material as a yellowish solid (89% yield). The purity of the compound was assessed by analytical HPLC on RP-C18 (gradient CH$_3$CN/H$_2$O in presence of 0.1% TFA, retention time 15 min). m.p. 196–198° C. with dec. $^1$H-NMR (CDCl$_3$): δ(ppm) 2.27–2.37 (1H, m, H2'), 2.42 and 2.44 (6H, 2×s, 2×Me), 2.79–2.85 (1H, m, H2"), 4.17 (2H, t, J=4.6 Hz, N—CH$_2$), 4.61–4.76 (3H, m, H4', H5', H5"), 5.62 (1H, d, J=6.2 Hz, H3'), 6.36 (1H, dd, J=5.6 and 8.0 Hz, H1'), 6.97 (1H, brs, NH—CH$_2$), 7.20–7.30 (m, 4H, aromatic), 7.86–7.96 (m, 5H, aromatic, H6), 8.61 (1H, brs, NH). m/z (MALDI-TOF MS) 636.8 (M+Na)+, C$_{30}$H$_{26}$F$_3$N$_3$O$_8$ requires 613.547.

3',5'-Di-O-p-toluoyl-5-N-trifluoroacetylaminopropyl-2'-deoxyuridine (1.3)

To a solution of the nucleoside (1.2) (2 g, 3.26 mmol) in THF (130 mL), 10% Pd/C (250 mg) was added and the mixture was hydrogenated (1 atm) at room temperature with vigorous stirring. After 12 hrs the reaction was complete (MALDI-TOF MS indicated the saturation of the triple bond to single bond). The suspension was filtered through celite and the cake washed with MeOH. The solvent was evaporated and the residue dissolved in CHCl$_3$ then washed with brine. The organic layer was dried over anhydrous Na$_2$SO$_4$ then evaporated to dryness. The crude material was purified by silica gel column chromatography (MeOH/CHCl$_3$ 0→2%) to give 1.85 g of pure material as a white solid (92% yield). $^1$H-NMR (CDCl$_3$): δH (ppm) 1.50–1.59 (2H, m, CH$_2$CH$_2$CH$_2$), 2.05–2.14 (2H, m, 5-CH$_2$), 2.27–2.37 (1H, m, H2'), 2.42 and 2.44 (6H, 2×s, 2×Me), 2.44–2.78 (1H, m, H2"), 3.17–3.24 (2H, m, N—CH$_2$), 4.55 (1H, brs, H5'), 4.63–4.68 (1H, m, H5"), 4.81–4.86 (1H, m, H4'), 5.64 (1H, d, J=6.2 Hz, H3'), 6.36 (1H, dd, J=5.4 and 8.8 Hz, H1'), 7.20–7.30 (4H, m, aromatic), 7.37 (1H, s, H6), 7.40 (1H, brs, NH—CH$_2$), 7.90–7.97 (4H, m, aromatic), 8.34 (1H, brs, NH). m/z (MALDI-TOF MS) 640.7 (M+Na)+, 656.7 (M+K)+, C$_{30}$H$_{30}$F$_3$N$_3$O$_8$ requires 617.579.

1-(3',5'-Di-O-p-toluoyl-2'-deoxy-β-D-ribofuranosyl)-4-(1,2,4-triazolyl)-5-N-trifluoroacetylaminopropyl-1H-pyrimidin-2-one (1.4)

To 1,2,4-triazole (3 g, 43.6 mmol previously dried by repeated coevaporations with anhydrous pyridine) suspended in anhydrous acetonitrile (75 mL) at 0° C., was added dropwise phosphoryl chloride (0.81 mL, 8.7 mmol) and the mixture was stirred for 10 min at 0° C. To this suspension freshly distilled triethylamine (7.4 mL, 52 mmol) was then added and the suspension stirred for 20 min at 0° C. and for a further 10 min at room temperature under nitrogen. After this time was added dropwise a solution of the nucleoside (1.3) (1.75 g, 2.91 mmol) in 40 mL of anhydrous acetonitrile and stirred at overnight at room temperature under nitrogen. The solvent was removed and the residue partitioned between chloroform (50 mL) and NaHCO$_3$ (2×30 mL), then brine (30 mL). The organic phase was dried with anhydrous sodium sulfate and then concentrated to dryness. The crude material was purified by silica gel column chromatography (EtOAc/Hexane 1:1→8:2) to give 0.96 g of off-white foam (50% yield). $^1$H-NMR (CDCl$_3$): δ(ppm) 1.57–1.69 (2H, m, CH$_2$CH$_2$CH$_2$), 2.28–2.37 (4H, m, H2', Me), 2.45 (3H, s, Me), 2.67–2.80 (2H, m, 5-CH$_2$), 3.20–3.32 (3H, m, N—CH$_2$, H2"), 4.65–4.72 (2H, m, H5', H5"), 4.90–4.94 (1H, m, H4'), 5.65 (1H, d, J=6.1 Hz, H3'), 6.38 (1H, d, J=5.9 Hz, H1'), 6.99 (1H, brs, NH—CH$_2$), 7.20–7.37 (4H, m, aromatic), 7.84 (2H, d, J=8.0, Hz aromatic), 7.98 (2H, d, J=8.0, Hz aromatic), 8.11 (1H, s, H6), 8.15 (1H, s, triazole), 9.30 (1H, s, triazole). m/z (MALDI-TOF MS) 692.2 (M+Na)+, 708.3 (M+K)+, C$_{32}$H$_{31}$F$_3$N$_6$O$_7$ requires 668.629.

1-(2'-deoxy-β-D-ribofuranosyl)piperidino[2,3-d]pyrimidine-2(1H)-one (1.5)

The nucleoside (1.4) (0.9 g, 1.34 mmol) was dissolved in 30 mL of methanolic ammonia and the solution vigorously stirred at room temperature. After 22 hrs stirring at room temperature a small amount of final product was detected by MALDI-TOF MS. The solvent was removed by rotary evaporation, the residue re-dissolved in MeOH and the solution refluxed for 1 hr (the formation of a new product having Rf 0.3 on TLC plate, run with MeOH/CHCl$_3$ 20%, was observed). The solvent was removed and the residue purified by silica gel column chromatography (MeOH/CHCl$_3$ 0→20%) to give 180 mg of pure compound as a white foam (50% yield). $^1$H-NMR (d$_6$-DMSO): δH (ppm) 1.67–1.72 (2H, m, CH$_2$CH$_2$CH$_2$), 1.90–2.07 (2H, m, H2', H2"), 2.40–2.45 (2H, m, 5-CH$_2$), 3.14–3.22 (2H, m, N—CH$_2$), 3.48–3.58 (2H, m, H5', H5"), 3.70–3.74 (1H, m, H4'), 4.17–4.21 (1H, m, H3'), 4.98 (1H, t, J=5.1 Hz, OH), 5.17 (1H, d, J=4.0 Hz, OH), 6.16 (1H, d, J=7.0 Hz, H1'), 7.57 (1H, s, H6), 7.83 (1H, brs, NH). m/z (MALDI-TOF MS) 268.8 (M+H)+, 290.8 (M+Na)+, 306.7 (M+K)+, C$_{12}$H$_{17}$N$_3$O$_4$ requires 267.285. UV (EtOH) λmax 286 nm (e=9.8×10$^3$) and 203 nm (e=24.0×10$^3$), λmin 236 nm (e=4.9×10$^3$), λsh 262 nm (e=7.4×10$^3$) and 222 nm (e=7.1×10$^3$); pH1 λmax 297 nm (e=13.9×10$^3$) and 219 nm (e=8.4×10$^3$), λmin 253 nm (e=2.2×10$^3$); pH12 λmax 281 nm (e=25.3×10$^3$).

1-(2'-deoxy-5'-triphosphate-β-D-ribofuranosyl)piperidino[2,3-d]pyrimidine-2(1H)-one (1.6)

The nucleoside (1.5) (100 mg, 0.374 mmol) and 1,8-bis(dimethylamino)naphthalene (Proton Sponge) (120 mg, 0.561 mmol, 1.5 eq) were dissolved in 2.2 mL of trimethylphosphate (dried with 4 Å molecular sieves) and the solution was cooled to −20° C. Phosphoryl chloride (70 μL, 0.748 mmol, 2 eq) was added and the mixture stirred with cooling (temperature was kept between −20 and −10° C.) for 4 hrs. After this time, to the purple solution tri-n-butylammonium pyrophosphate (3.74 mL of 0.5 M solution in anhydrous DMF, 1.87 mmol, 5 eq) was added followed by tri-n-butylamine (0.37 mL, 1.57 mmol, 4.2 eq) and the mixture was stirred at −20° C. for 3 mins. Then 25 mL of 0.4 M TEAB solution was added and the mixture stirred at room temperature for 10 mins. Water and TEAB were removed by rotary evaporation and to the residue diethyl ether (30 mL) was added. The solvent was decanted and the gummy residue was washed once again with 30 mL of diethyl ether. After decanting the residue was dried to give 1.7 g of a gummy crude material. The crude material was purified by ion exchange chromatrography (0–100% B over 90 min. B=0.3M trimethylammonium bicarbonate, 3 ml/min) then the product further purified by reverse phase separation using a Waters Sep-Pak C18 cartridge eluting with 20% acetonitrile/0.1M triethylammonium bicarbonate to give the title compound. $^1$H-NMR (D$_2$O) δ(ppm) 1.68–1.72 (2H, m, CH$_2$CH$_2$CH$_2$), 2.16 (2H, m, H2',H2"), 2.45 (2H, m, 5-CH$_2$), 3.16 (2H, m, N—CH$_2$), 3.16 (2H, m, H5',H5"), 4.02 (1H, m, H4'), 4.17–4.12 (1H, m, H3'), 6.07 (1H, m, H1'), 7.60 (1H, s, H6). $^{31}$P-NMR (D$_2$O): δ(ppm) −10.46 (d), −11.62 (d), −23.33 (t)

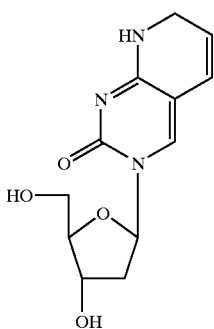

The nucleoside (1.7) and its triphosphate derivative can be made by an analogous route by carrying out a Lindlar reduction on the nucleoside (1.2) and then repeating the synthetic steps above. The experimental for the Lindlar reduction is detailed below.

Dissolve 1.5 g of (1.2) in 75 mL of methanol in a Parr hydrogenation flask. With a pasteur pippete, add 5 drops of quinoline and 0.5 g of Pd/CaCO$_3$ (Lindlar catalyst-Aldrich) (0.3 equivalents by weight). Put the flask to a Parr hydrogenation apparatus, evacuate the air with hydrogen three times using a water aspirator, regulate the hydrogen pressure to 30 psi and shake the flask overnight. The reaction is checked for completion by TLC (20% MeOH/Chloroform). When the reaction has gone to completion the catalyst is filtered off, wash the filter with methanol and coevaporate the filtrate with 50 g of silica gel. The product is the purified by gradient flash chromatography using the following 10, 15, 20, 25% MeOH/Chloroform which afforded 1.2 g of the required olefinic intermediate as an intermediate en route to (1.7), 70% yield.

EXAMPLE 2

Synthesis of 3-(2-deoxy-β-D-erythro-pentofuranosyl)-6-(butyl-4-N-2,2,2-trifluoro-acetamide)-furano[2,3-d]pyrimidin-2-one (2.6)

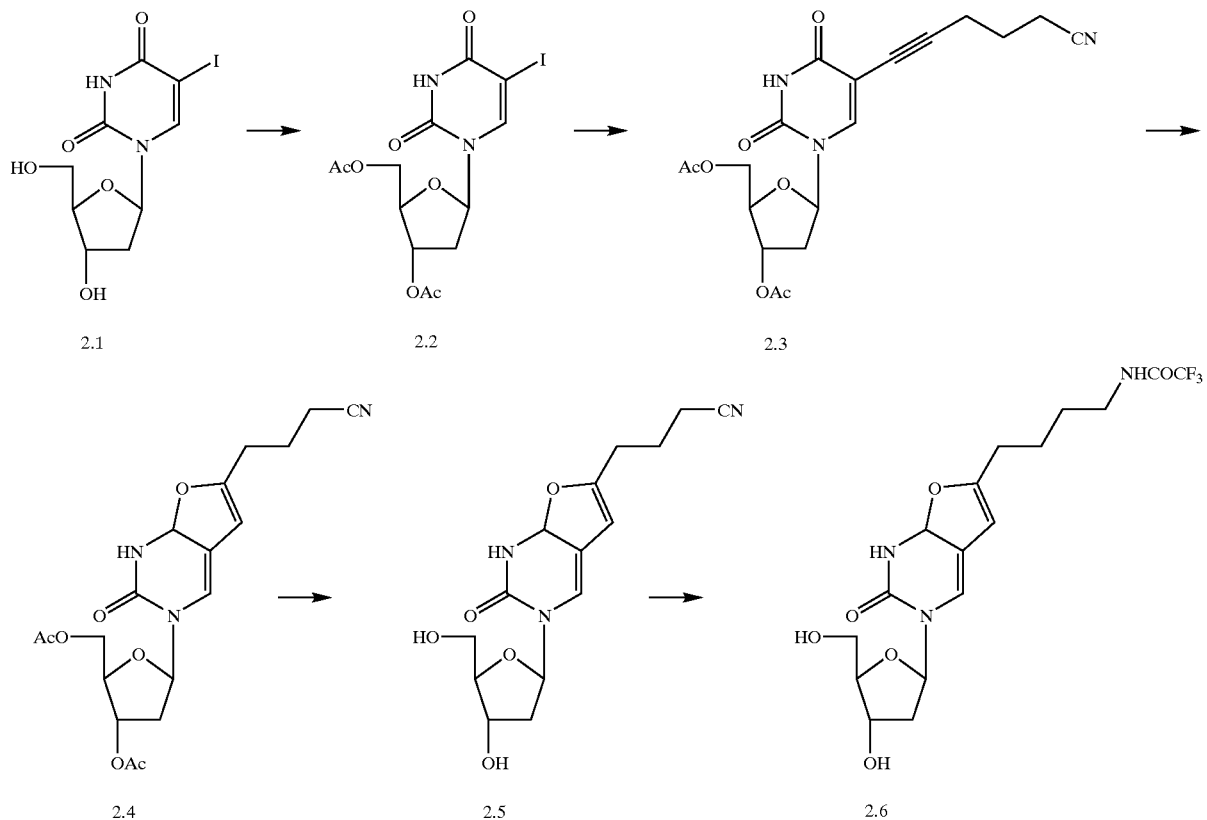

3',5'-Di-O-acetyl-5-iodo-2'-deoxyuridine (2.2)

To 5-iodo-2'-deoxyuridine (2.1) (70.8 g, 200 mmol, 1 eq) in an 500 mL Erlenmeyer flask was added acetic acid (72 g, 68.7 mL, 1200 mmol, 6 eq) and acetic anhydride (51 g, 47.1 mL, 500 mmol, 2.5 eq). In a test tube at 0° C., the catalyst for the reaction was prepared by adding HClO$_4$ (0.5 mL) over acetic anhydride (2 mL). Five drops of the catalyst were added into the Erlenmeyer flask at 0° C. with stirring. The reaction mixture was brought to room temperature and stirred for 4 hours where upon a thick white precipitate formed. The Erlenmeyer flask was filled with ether and stirred vigorously for 30 minutes. The white precipitate was filtered and the white cake was washed with ether (500 mL).

The product was dried in the vacuum oven overnight to afford (2.2) (90.1 g, 95%) $^1$H-NMR (CDCl$_3$) δ(ppm) 9.40 (bs, 1 H, exchangeable, NH), 7.78 (s, 1 H, H-6), 6.18 (dd, J=8.10 Hz, 1 H, H-1'), 5.05 (m, 1 H, H-3'), 4.07–4.25 (m, 3 H, H-6), 4', 5'), 2.35 (m, 1 H, H-2'$_b$), 1.85–2.12 (m, 7 H, 2×CH$_3$, H-2'$_a$)

3',5'-Di-O-acetyl-5-(pentyn-5-Cyano)-2'-deoxyuridine (2.3)

This compound was prepared from (2.1) (4.73 g, 10 mmol, 1 eq) in a similar manner as (2.4) except the reaction mixture was stirred overnight at room temperature to afford (2.3) (3.04 g, 75%): UV (MeOH) λ$_{max}$ 289 nm; $^1$H-NMR (CDCl$_3$) δ9.27 (s, 1 H, exchangeable, H—NH), 7.80 (s, 1 H, H-6), 6.30 (t, J=6.55 Hz, 1 H, H-1'), 5.25 (m, 1 H, H-3'),), 4.40 (m, 3 H, H-4', 5'), 2.60 (m, 5 H, H-2'$_β$, C≡CCH$_2$CH$_2$CH$_2$CN), 2.10 (m, 7 H, H-2'$_α$, 2×CH$_3$), 1.95 (m, 2 H, H—CH$_2$CH$_2$CH$_2$). This compound can be cyclised to (2.4) by refluxing with a catalytic amount of CuI and ten equivalents of triethylamine in methanol.

6-Butyronitrile-3-(3,5-Di-O-acetyl-β-D-erythro-pentofuranosyl)furano[2,3-d]pyrimidin-2-one (2.4)

Triethylamine (3.04 g, 4.2 mL, 30 mmol, 2 eq) was added to a stirred solution of (2.2) (7.1 g, 15 mmol, 1 eq), Pd[P(C$_6$H$_5$)$_3$]$_4$ (1.73 g, 1.5 mmol, 0.1 eq), CuI (0.57 g, 3 mmol, 0.2 eq) and hexynenitrile (2.79 g, 30 mmol, 2 eq) in dry DMF (50 mL) and the reaction mixture was then stirred overnight at 55° C. under an inert atmosphere. To the reaction mixture was then added the bicarbonate form of AG1×8 resin to remove triethylammonium hydroiodide, CHELEX resin to remove metal cations and activated charcoal to remove colour. After filtration on Celite a slightly yellow solution was produced. Solvent removal under high vacuum gave a dark residue which was dissolved in methanol and coevaporated with silica gel (75 g). Flash chromatography with 10% methanol/chloroform as eluant afforded (2.3) (3.9 g, 64%) UV (MeOH) λ$_{max}$ 324 nm; $^1$H-NMR (CDCl$_3$) δ(ppm) 8.22 (s, 1 H, H-6), 6.30 (t, J=6.55 Hz, 1 H, H-1'), 6.25 (s, 1 H, HC=C(O)CH$_2$), 5.20 (m, 1 H, H-3'), 4.40 (m, 3 H, H4', 5'), 2.92 (m, 3H, H-2'$_b$, HC=C(O)CH$_2$CH$_2$), 2.43 (t, 2 H, H—CH$_2$CH$_2$CN), 2.05–2.10 (m, 9 H, H-2'$_a$, 2×CH$_3$, CH$_2$CH$_2$CH$_2$)

6-Butyronitrile-3-(2-deoxy-β-D-erythro-pentofuranosyl)furano[2,3-d]pyrimidin-2-one (2.5)

To 2 M KOH solution (1.6 mL) was added a solution of (2.4) (0.61 g, 1.5 mmol) in methanol (10 mL) and the mixture stirred for 4 minutes. TLC (20% methanol/chloroform) showed the reaction had gone completion. After neutralization with 1 N HCl the solvents were removed under reduced pressure. The resulting residue was dissolved in methanol and any remaining insoluble salt filtered out. Removal of the solvent provided crude (2.5) (0.48 g, 97%) UV (MeOH) λ$_{max}$ 324 nm; $^1$H-NMR (d$_6$-DMSO) δ(ppm) 8.75 (s, 1H, H-6), 6.57 (s, 1 H, H—CH=C(O)CH$_2$), 6.30 (t, J=6.55 Hz, 1 H, H-1'), 5.33 (m, 1 H, exchangeable, H—OH), 5.18 (m, 1 H, H—OH), 4.23 (m, 1 H, H-3'), 3.92 (m, 1 H, H4'), 3.68 (m, 2 H, H-5'), 2.80 (t, J=, 2 H, H—CH=C(O)CH$_2$CH$_2$), 2.60 (t, 2H, H—CH$_2$CH$_2$CN), 2.40 (m, 2 H, H-2'$_b$), 2.05 (m, 1 H, H-2'$_a$), 1.92 (m, 2 H, H—CH$_2$CH$_2$CN)

2,2,2-Trifluoro-N-(3-(2-deoxy-β-D-erythro-pentofuranosyl)furano[2,3-d]pyrimidin-2-one-6-Butyl)-acetamide (2.6)

A solution of (2.5) (0.1 g, 0.32 mmol) in methanol (15 mL) and Raney-Ni hydrogenation catalyst (1 g) were loaded into a Parr apparatus and stirred under hydrogen (p=25 psi) for 4 hours. TLC (20% methanol/chloroform) shows reaction completion. The reaction mixture was filtered through Celite. To the filtrate was then added ethyl trifluoroacetate (1 mL) and triethylamine (0.5 mL) and the mixture left to stir for 4 hours. Solvent evaporation and chromatography (15–20% methanol/chloroform) afforded (2.6) (81 mg, 60%) UV (MeOH) λ$_{max}$ 324 nm; $^1$H-NMR (d$_6$-DMSO) δ(ppm) 9.40 (bs, 1 H, exchangeable, H—NHCOCF$_3$) 8.75 (s, 1 H, H-6), 6.47 (s, 1 H, H—CH=C(O)CH$_2$), 6.18 (t, J=6.55 Hz, 1 H, H-1'), 5.33 (m, 1 H, exchangeable, H—OH), 5.18 (m, 1 H, H—OH), 4.23 (m, 1 H, H-3'), 3.92 (m, 1 H, H4'), 3.68 (m, 2 H, H-5'),), 3.20 (m, 2 H, H—CH$_2$CH$_2$NH), 2.62 (t, J=, 2 H, H—CH=C—O—CH$_2$CH$_2$), 2.40 (m, 2 H, H-2'$_b$), 2.05 (m, 1 H, H-2'$_a$), 1.60–1.80 (m, 4 H, H—CH$_2$CH$_2$CH$_2$CH$_2$NH)

EXAMPLE 3

Synthesis of 6-methylamine-3-(5-triphospho-2-deoxy-β-D-erythro-pentofuranosyl)furano[2,3-d]pyrimidin-2-one) (3.3a) and 5-Carboxyfluoresceinyl-(6-methylamine-3-(5-triphosphate-2-deoxy-β-D-erythro-pentofuranosyl)furano[2,3-d]pyrimidin-2-one) (3.3b)

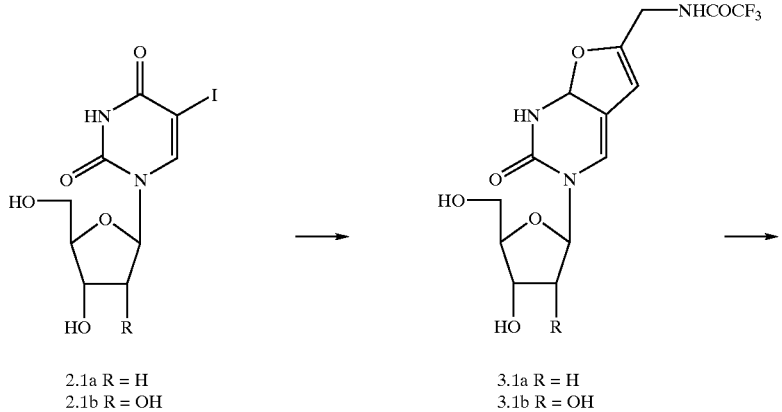

2.1a R = H
2.1b R = OH 3.1a R = H
3.1b R = OH

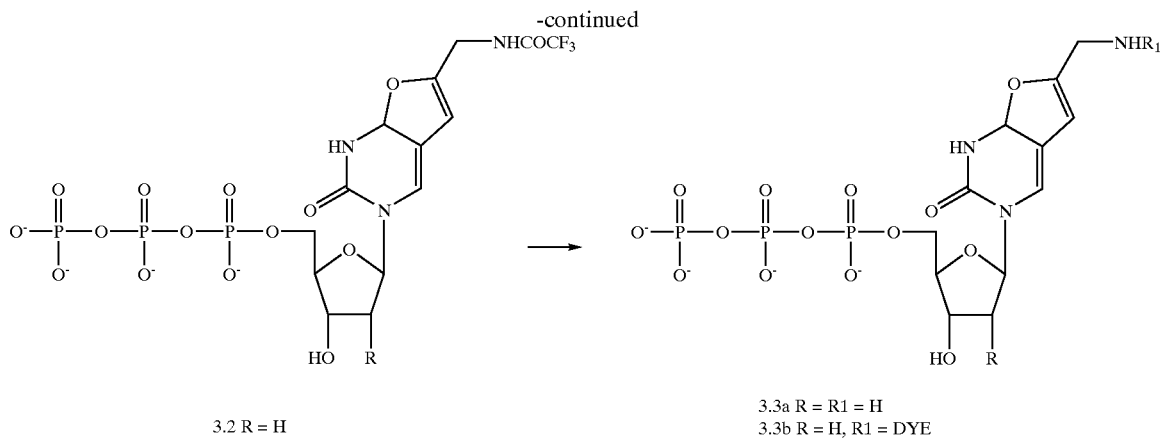

3.2 R = H 3.3a R = R1 = H
3.3b R = H, R1 = DYE 2,2,2-Trifluoro-N-(3-(2-deoxy-β-D-erythro-pentofuranosyl)furano[2,3-d]pyrimidin-2-one-6-methyl)-acetamide (3.1a)

Triethylamine (3.04 g, 4.2 mL, 30 mmol, 1.5 eq) was added to a stirred solution of 5-iodo-2'-deoxyuridine (7.1 g, 20 mmol, 1 eq), Pd[P(C$_6$H$_5$)$_3$]$_4$ (1.16 g, 1 mmol, 0.05 eq), CuI (0.38 g, 2 mmol, 0.1 eq) and 2,2,2-trifluoro-N-propargyl-acetamide (4.53 g, 30 mmol, 1.5 eq) in dry DMF (75 mL) and the resulting reaction mixture was then stirred for two days at 55° C. under inert atmosphere. Isolation and purification of the product as described for the preparation of (2.4), yielded (3.1a) (4.2 g, 56%) UV (MeOH) $\lambda_{max}$ 324 nm; $^1$H-NMR (d$_6$-DMSO) δ(ppm) 10.07 (s, 1 H, exchangeable, H—NH—COCF$_3$), 8.78 (s, 1 H, H-6), 6.63 (s, 1 H, H—CH═C(O)CH$_2$), 6.18 (t, J=6.55 Hz, 1 H, H-1'), 5.00–5.3 (bm, 2H, exchangeable, 2×OH), 4.48 (m, 2H, H—CH$_2$—NH), 4.23 (m, 1 H, H-4'), 3.95 (m, 1 H, H-3'), 3.63 (m, 2 H, H-5'), 2.40 (m, 1 H, H-2'$_b$), 2.07 (m, 1 H, H-2'$_a$)

2,2,2-Trifluoro-N-(3-(2-deoxy-β-D-erythro-pentofuranosyl)furano[2,3-d]pyrimidin-2-one-6-methyl)-acetamide (3.1b)

Triethylamine (0.46 g, 0.63 mL, 4.5 mmol, 1.5 eq) was added to a stirred solution of (2.1b) (1.11 g, 3 mmol, 1 eq), Pd[P(C$_6$H$_5$)$_3$]$_4$ (0.35 g, 0.3 mmol, 0.1 eq), CuI (0.12 g, 0.6 mmol, 0.2 eq) and 2,2,2-trifluoro-N-propargyl-acetamide (0.55 g, 3.6 mmol, 1.2 eq) in dry DMF (25 mL) and the resultant reaction mixture was then stirred for two days at 55° C. under an inert atmosphere. Isolation and purification of the product as described for the preparation of (2.4), yielded (3.1b) (0.62 g, 53%): UV (MeOH) $\lambda_{max}$ 324 nm; $^1$H-NMR (d$_6$-DMSO) δ(ppm) 10.08 (s, 1 H, exchangeable, H—NH—COCF$_3$), 8.90 (s, 1 H, H-6), 6.63 (s, 1 H, H—CH═C(O)CH$_2$), 5.87 (d, J=6 Hz, 1 H, H-1'), 5.58 (m, 1 H, exchangeable, H—OH), 5.25 (m, 1 H, exchangeable, H—OH), 5.00 (m, 1 H, exchangeable, H—OH), 4.48 (m, 2 H, H—CH$_2$—NH), 4.00 (m, 3H, H-4', 3', 2'), 3.86 (m, 1H, H-5'$_b$), 3.68 (m, 1 H, H-5'$_a$)

2,2,2-Trifluoro-N-(3-(5-triphospho-2-deoxy-β-D-erythro-pentofuranosyl)furano[2,3-d]pyrimidin-2-one-6-methyl)-acetamide (3.2)

The nucleoside (3.1a) (1 g, 2.7 mmol, 1 eq) was dissolved in triethylphosphate (50 mL) and the solution cooled to 0° C. Phosphorus oxychloride (0.163 g, 0.37 mL, 4 mmol) was added dropwise and the reaction mixture stirred at 0° C. under inert atmosphere for three hours. TLC on silica gel (i-Pr—OH/NH$_4$OH/H$_2$O-6/3/1) showed reaction completion to the monophosphate stage. Tributylamine (2.5 g, 3.25 mL, 13.5 mmol, 5 eq) and di-tributylammonium pyrophosphate 0.5M solution in dry DMF (27 mL, 13.5 mmol, 5 eq) were simultaneously added at 0° C. The resulting reaction mixture was stirred at 0° C. for five minutes then ten minutes at room temperature before quenching with 1 M triethylamine bicarbonate (TEAB) buffer (100 mL) and leaving to stir overnight at room temperature. After solvent removal, the reaction mixture was dissolved in water and applied to a SEPHADEX resin (1 L column). Elution with 4 L TEAB buffer in gradient mode from 0.05 M TEAB to 1 M TEAB afforded (3.2). The product was further purified on HPLC using a reverse phase C18 column using 0.1 mTEAB and 25% MeCN in 0.1M TEAB as eluants over a 30 min gradient (0.3 g, 14%): UV (H$_2$O) $\lambda_{max}$ 324 nm; $^{31}$P-NMR (D$_2$O) δ(ppm) −6.00 (d, J=21.06 Hz), −12.50 (d, J=19.53 Hz), −22.2 (t, J=20.45 Hz)

6-Methylamine-3-(5-triphospho-2-deoxy-β-D-erythro-pentofuranosyl)furano[2,3-d]pyrimidin-2-one) (3.3a)

Hydrolysis of (3.2) (10.9 mg, 3 mL sol 4.423 mM in water) with 2.5 M sodium carbonate buffer (3 mL) at room temperature for three hours and purification of the crude product on HPLC using a C18 column and the same gradient system as above, afforded (3.3a) (5.9 mg, 82%): UV (H$_2$O) $\lambda_{max}$ 324 nm; $^{31}$P-NMR (D$_2$O) δ(ppm) −4.00 (d, J=21.06 Hz), −10.20 (d, J=19.53 Hz), −19.50 (t, J=20.45 Hz)

5-Carboxyfluoresceinyl-(6-methylamine-3-(5-triphospho-2-deoxy-β-D-erythro-pentofuranosyl)furano[2,3-d]pyrimidin-2-one) (3.3b)

5-Carboxyfluorescein-N-hydroxysuccinimide ester (FAM-NHS ester) (1.7 mg, 1.25 eq) dissolved in 0.5 mL dry DMF was added to (3.2) (0.84 mg, 14.8 mM, 1 eq) dissolved in 0.25 M sodium carbonate/sodium bicarbonate buffer (1 mL) at pH=8.5 and the resulting mixture stirred at room temperature for three hours. TLC on silica gel (i-Pr—OH/NH$_4$OH/H$_2$O -6/3/1) showed reaction completion. Purification on a short plug of a silicagel column followed by reverse phase HPLC on C18 column afforded (3.3b). UV (H$_2$O) $\lambda_{max}$ 324 nm 493 nm

EXAMPLE 4

Synthesis of 6-methyl-N-(6-amino)-caproamide-3-(5-triphospho-2-deoxy-β-D-erythro-pentofuranosyl)furano[2,3-d]pyrimidin-2-one (4.3a) and 5-FAM-(6-methyl-N-(6-amino)-caproamide-3-(5-triphospho-2-deoxy-β-D-erythro-pentofuranosyl)furano[2,3-d]pyrimidin-2-one) (4.3b)

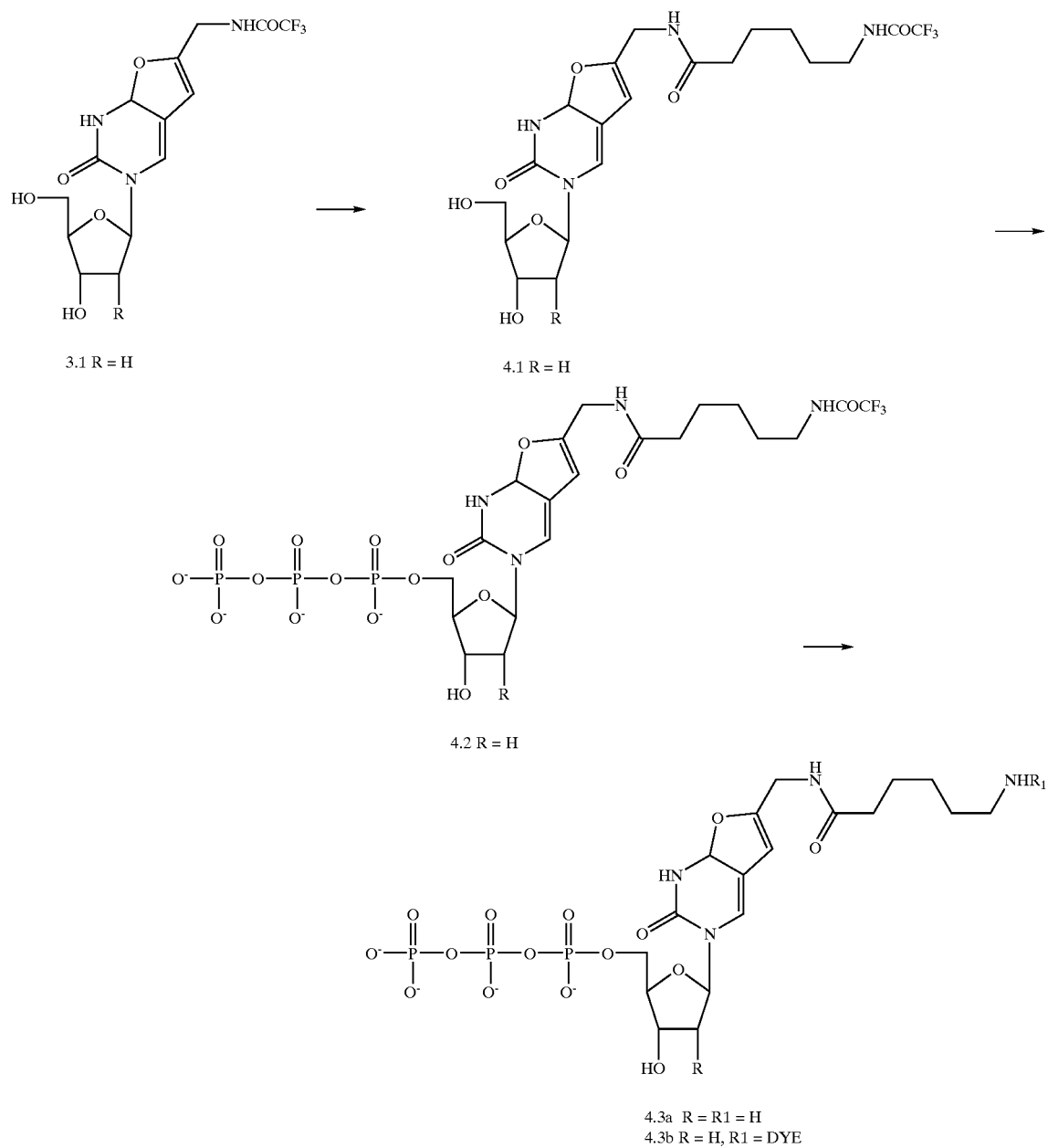

4.3a R = R1 = H
4.3b R = H, R1 = DYE 2,2,2-Trifluoro-(6-methyl-N-(6-amino)-caproamide-3-(2-deoxy-β-D-erythro-pentofuranosyl)furano[2,3-d]pyrimidin-2-one)-acetamide (4.1)

Treatment of (3.1a) (0.37 g, 1 mmol, 1 eq) with 2.5 M sodium carbonate buffer (10 mL) for three hours followed by addition of 2,2,2-Trifluoro-N-(6-amino-N-Hydroxysuccinimide caproate)-acetamide (0.48 g, 1.5 mmol, 1.5 eq) dissolved in 3 mL of dry DMF, afforded after chromatography on silicagel (15% methanol/chloroform as eluent) the desired compound (4.1) (0.27 g, 55%): UV (MeOH) $\lambda_{max}$ 324 nm; $^1$H-NMR (d$_6$-DMSO) δ(ppm) 9.37 (bs, 1 H, exchangeable, H—NH—COCF$_3$), 8.74 (s, 1 H, H-6), 8.33 (s, 1 H, exchangeable, H—CH$_2$NH—COCH$_2$), 6.50 (s, 1 H, H—CH=C(O)CH$_2$), 6.12 (t, J=6.45 Hz, 1H, H-1'), 5.27 (m, 1 H, exchangeable, H—OH), 5.11 (m, 1 H, exchangeable, H—OH), 4.21 (m, 3 H, H-3', OCCH$_2$NHCO), 3.88 (m, 1 H, H4'), 3.65 (m, 2 H, H-5'), 3.16 (m, 2 H, H—CH$_2$NHCOCF$_3$), 2.35 (m, 1 H, H-2'$_b$), 2.15 (t, J=7.27

Hz, 2 H, H—CH$_2$CONH), 2.00 (m, 1 H, H-2'$_a$), 1.5 (m, 4 H, H—CH$_2$CH$_2$CH$_2$CH$_2$CH$_2$), 1.26 (m, 2 H, H—CH$_2$CH$_2$CH$_2$CH$_2$CH$_2$)

2,2,2-Trifluoro-N-(6-methyl-N-(6-amino)-caproamide-3-(5-triphospho-2-deoxy-β-D-erythro-pentofuranosyl)furano[2,3-a]pyrimidin-2-one)-acetamide (4.2)

This compound was prepared from (4.1) (0.169 g, 0.35 mmol, 1 eq) in a similar manner as (3.2) to afford (4.2) (70 mg, 22%): UV (H$_2$O) $\lambda_{max}$ 324 nm; $^{31}$P-NMR (D$_2$O) δ(ppm) −4.00 (d, J=21.06 Hz), −10.20 (d, J=19.53 Hz), −19.50 (t, J=20.45 Hz)

6-Methyl-N-(6-amino)-caproamide-3-(5-triphospho-2-deoxy-β-D-erythro-pentofuranosyl)furano[2,3-d]pyrimidin-2-one (4.3a)

This compound was prepared from (4.2a) (20 mg, 21.5 mM, 1 eq) in a similar manner as (3.3a) to afford (4.3a) (15 mg, 84%): UV (H$_2$O) $\lambda_{max}$ 324 nm; $^{31}$P-NMR (D$_2$O) δ(ppm) −4.00 (d, J=21.06 Hz), −10.20 (d, J=19.53 Hz), −19.50 (t, J=20.45 Hz)

5-FAM-(6-methyl-N-(6-amino)-caproamide-3-(5-triphospho-2-deoxy-β-D-erythro-pentofuranosyl)furano[2,3-d]pyrimidin-2-one) (4.3b)

This compound was prepared from (4.2) (1.7 mg, 20.3 mM, 1 eq) in a similar manner as (3.3b) to afford (4.3b) (0.91 mM, 5%): UV (H$_2$O) $\lambda_{max}$ 324 nm 493.8 nm

EXAMPLE 5

Synthesis of 2,2,2-Trifluoro-N-(3-(2-deoxy-β-D-erythro-pentofuranosyl)furano-pyrimidin-2-one-6-methyl)-acetamide (5.1)

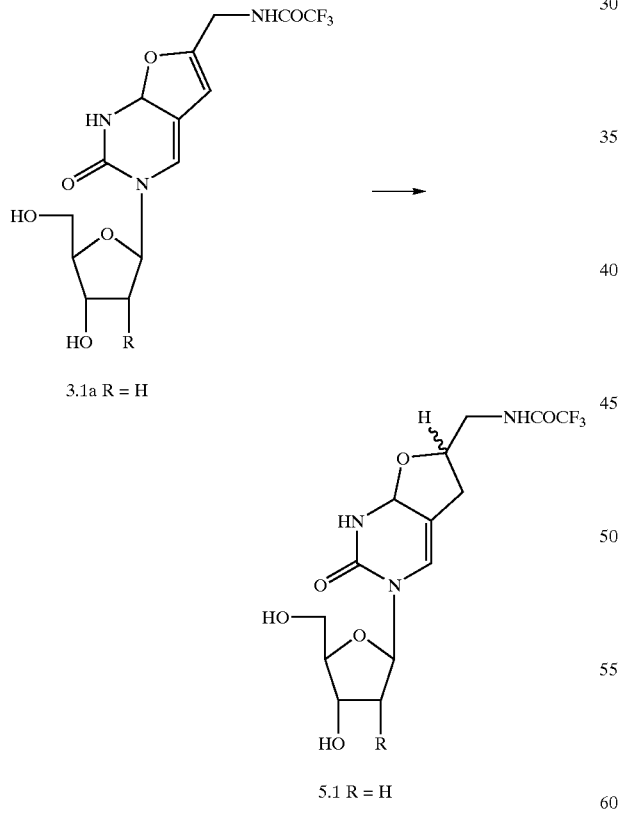

2,2,2-Trifluoro-N-(3-(2-deoxy-β-D-erythro-pentofuranosyl) 5,6-dihydro-furano-pyrimidin-2-one-6-methyl)-acetamide (5.1)

A solution of (3.1a) (0.19 g, 0.5 mmol) in methanol (50 mL) and 5%Pd/C hydrogenation catalyst (0.19 g) were loaded into a Parr hydrogenation apparatus and stirred under hydrogen atmosphere (25 psi) for two hours. TLC on silica gel (15% methanol/chloroform as eluent) showed reaction completion. The reaction mixture was filtered and the catalyst washed three times (50 mL) with hot methanol. Solvent evaporation afforded (5.1) as a diastereomeric mixture (0.16 g, 85%). UV (MeOH) λmax 271 nm; $^1$H-NMR (d$_6$-DMSO) δ(ppm) 9.80 (bs, 1H, exchangeable, NH), 9.4 (bs, 1H, exchangeable), 8.18 (s, 1 H), 7.70 (s, 1H) 6.18(m, 2H), (4.80–5.40 (m, 4H, exchangeable), 4.20 (m, 2 H), 3.80 (m, 2H), 3.40 (m, 2 H), 3.40, 3.25 (m, 4H), 2.80 (m, 1H), 1.90–2.4 and 1.70 (m, 5H)

EXAMPLE 6

Synthesis of 6-Butyronitrile-3-(2-deoxy-β-D-erythro-pentofuranosyl)pyrrolo[2,3-d]pyrimidin-2-one (6.1)

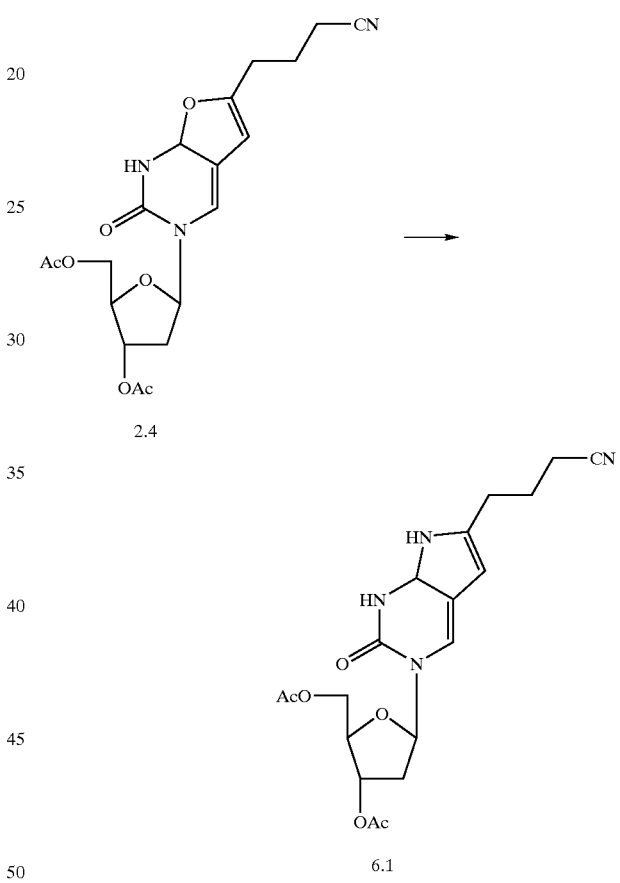

6-Butyronitrile-3-(2-deoxy-β-D-erythro-pentofuranosyl) pyrrolo[2,3-d]pyrimidin-2-one (6.1)

A solution of (2.1) (0.5 g, 1.24 mmol) in concentrated ammonium hydroxide (25 mL) was stirred overnight. TLC (30% methanol/chloroform) showed the reaction was complete. Purification on silicagel by flash chromatography (15–25% methanol/chloroform) afforded (6.1) (0.324 g, 82.8%) UV (MeOH) $\lambda_{max}$ 335 nm; $^1$H-NMR (d$_6$-DMSO) δ(ppm) 11.17 (bs, 1H, exchangeable, NH), 8.55 (s, 1 H, H-6), 6.25 (t, J=6.44 Hz, 1 H, H-1'), 6.00 (s, 1 H, CH═C (NH)CH$_2$), 5.25 (m, 1H, exchangeable, H—OH), 5.10 (m, 1 H, exchangeable, H—OH), 4.28 (m, 1 H, H-3'), 3.90 (m, 1 H, H4'), 3.68 (m, 2 H, H-5'), 2.69 (t, J═, 2H, H—HC═C (O)CH$_2$CH$_2$), 2.53 (t, 2 H, H—CH$_2$CH$_2$CN), 2.38 (m, 1 H, H-2'$_b$), 2.00 (m, 1 H, H-2'$_a$)

EXAMPLE 7

Synthesis of 2,2,2-Trifluoro-N-(3-(β-D-erythro-pentofuranosyl)pyrrolo[2,3-d]pyrimidin-2-one-6-methyl)-acetamide (7.1b)

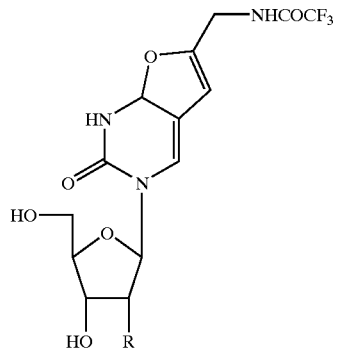

3.1 R = H
3.1b R = OH

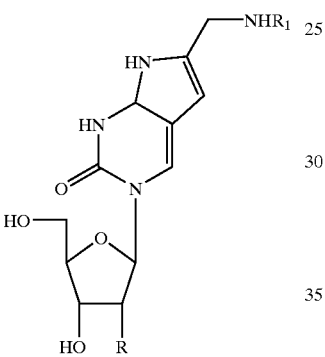

7.1a R = R1 = H
7.1b R = H, R1 = COCF₃

2,2,2-Trifluoro-N-(3-(β-D-erythro-pentofuranosyl)pyrrolo[2,3-d]pyrimidin-2-one-6-methyl)-acetamide (7.1b)

Overnight treatment of (3.1) (0.37 g, 1 mmol, 1 eq) with concentrated ammonium hydroxide solution (10 mL) at room temperature afforded after solvent evaporation compound (7.1a). Ethyl trifluoroacetate (1 mL) and triethylamine (0.1 mL) were added to a methanolic solution of crude (7.1a) and the reaction mixture stirred for 4 hours at room temperature. Solvent removal and flash chromatography with 15% methanol/chloroform as eluent afforded (7.1b) (0.286 g, 76%): UV (MeOH) $\lambda_{max}$ 335 nm; $^1$H-NMR (d$_6$-DMSO) δ(ppm) 11.50 (bs, 1 H, exchangeable, H—NH-pyrrol ring), 10.18 (bs, 1 H, exchangeable, H—NH—COCF₃), 8.70 (s, 1 H, H-6), 6.25 (t, J=6.55 Hz, 1 H, H-1'), 6.08 (s, 1 H, H—CH=C(NH)CH₂),), 5.25 (m, 1H, exchangeable, H—OH), 5.10 (m, 1 H, exchangeable, H—OH), 4.27 (m, 3 H, H—=C(NH)CH₂COCF₃, and 4'), 3.90 (m, 1 H, H-3'), 3.68 (m, 2H, H-5'), 2.38 (m, 1 H, H-2'$_b$), 2.07 (m, 1 H, H-2'$_a$)

EXAMPLE 8

Synthesis of 6-methylamine-3-(5-triphospho-2-deoxy-β-D-erythro-pentofuranosyl)pyrrolo[2,3-d]pyrimidin-2-one) (8.1)

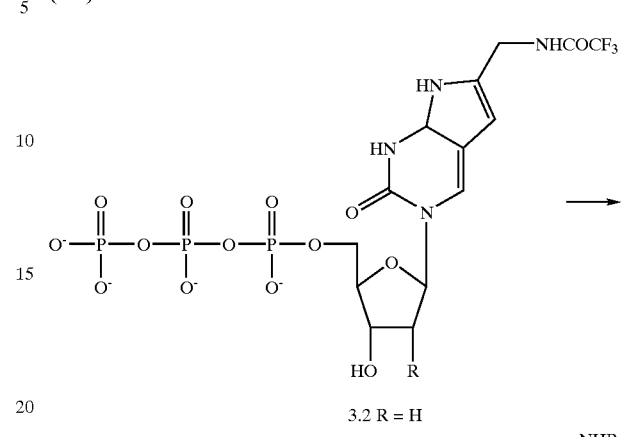

3.2 R = H

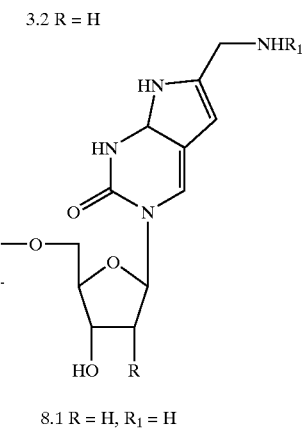

8.1 R = H, R₁ = H 6-methylamine-3-(5-triphospho-2-deoxy-β-D-erythro-pentofuranosyl)pyrrolo[2,3-d]pyrimidin-2-one) (8.1)

Treatment of (3.2) (10.9 mg, 3 mL sol 4.423 mM in water) with concentrated ammonium hydroxide solution (3 mL) at room temperature for three hours and purification on HPLC (C₁₈) of the crude product, afforded (8.1) (0.6 mg, 8%): UV (H₂O) $\lambda_{max}$ 268 nm 335 nm

EXAMPLE 9

Synthesis of 2,2,2-Trifluoro-(6-methyl-N-(6-amino)-caproamide-3-(2-deoxy-β-D-erythro-pentofuranosyl)pyrrolo[2,3-d]pyrimidin-2-one)-acetamide (9.1)

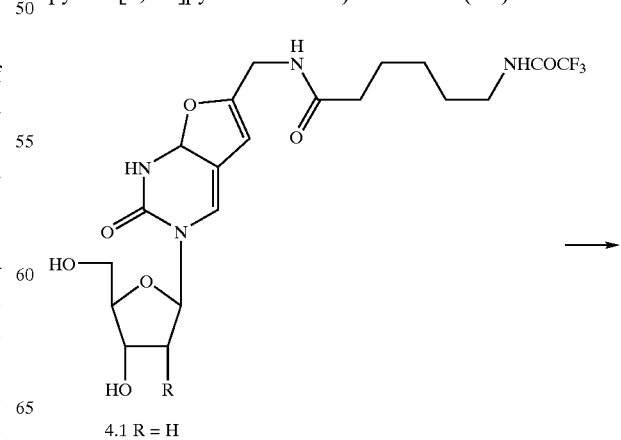

4.1 R = H

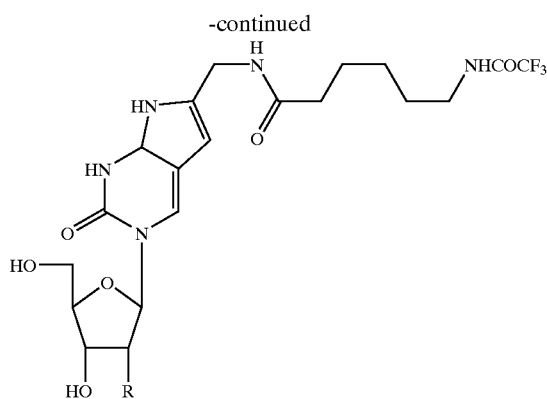

9.1 R = H 2,2,2-Trifluoro-(6-methyl-N-(6-amino)-caproamide-3-(2-deoxy-β-D-erythro-pentofuranosyl)pyrrolo[2,3-d]pyrimidin-2-one)-acetamide (9.1)

This compound was prepared from (4.1a) (0.1 g, 0.2 mmol, 1 eq) in a similar manner as (7.1b) to afford (9.1) (0.074 g, 76%): UV (MeOH) $\lambda_{max}$ 335 nm; $^1$H-NMR (d$_6$-DMSO) δ(ppm) 9.37 (bs, 1 H, exchangeable, H—NH—COCF$_3$), 9.36 (bs, 1 H, exchangeable, H—N=C—NH—C(CH$_2$)=CH), 8.59 (s, 1 H, H-6), 8.28 (s, 1 H, exchangeable, H—CH$_2$NH—COCH$_2$), 6.25 (dd, J=8.10 Hz, 5.4 Hz, 1 H, H-1'), 6.02 (s, 1 H, H—CH=C(NH)CH$_2$), 5.27 (m, 1 H, exchangeable, H—OH), 5.11 (m, 1 H, exchangeable, H—OH), 4.21 (m, 3 H, H-3', OCCH$_2$NHCO), 3.88 (m, 1 H, H-4'), 3.65 (m, 2 H, H-5'), 3.16 (m, 2 H, H—CH$_2$NHCOCF$_3$), 2.35 (m, 1 H, H-2'$_b$), 2.15 (t, J=7.27 Hz, 2 H, H—CH$_2$CONH), 2.00 (m, 1 H, H-2'$_a$), 1.5 (m, 4 H, H—CH$_2$CH$_2$CH$_2$CH$_2$CH$_2$), 1.26 (m, 2 H, H—CH$_2$CH$_2$CH$_2$CH$_2$CH$_2$)

EXAMPLE 10

Synthesis of dye conjugates of 6-methyl-N-(6-amino)-caproamide-3-(5-triphospho-2-deoxy-β-D-erythro-pentofuranosyl)pyrrolo[2,3-d]pyrimidin-2-one (10.1a)

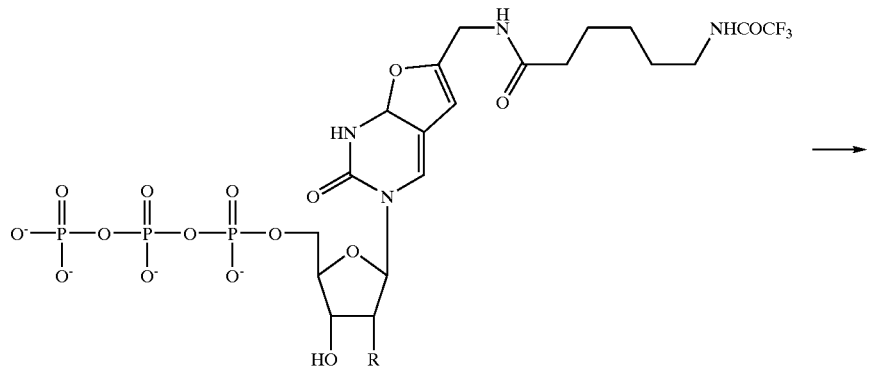

4.2 R = H

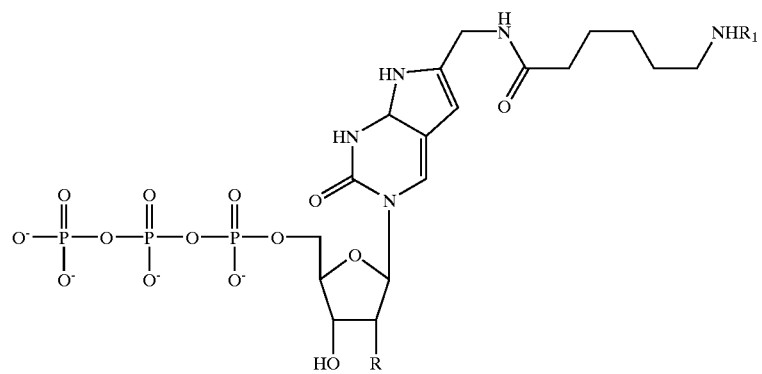

10.1a R = R1 = H
10.1b R = H, R1 = 5FAM
10.1c R = H, R1 = Cy5

6-methyl-N-(6-amino)-caproamide-3-(5-triphospho-2-deoxy-β-D-erythro-pentofuranosyl)pyrrolo[2,3-d]pyrimidin-2-one (10.1a)

This compound was prepared from (4.2) (30 mg, 35.8 mM, 1 eq) in a similar manner as (8.1a) to afford (10.1a) (20 mg, 24.3 mM, 68%): UV (H$_2$O) $\lambda_{max}$ 335 nm 5-FAM-(6-methyl-N-(6-amino)-caproamide-3-(5-triphospho-2-deoxy-β-D-erythro-pentofuranosyl)pyrrolo[2,3-d]pyrimidin-2-one) (10.1b)

This compound was prepared from (10.1a) (6.5 mg, 7.8 mM, 1 eq) in a similar manner as (8.1b) to afford (10.1b) (1.88 mM, 24%): UV (H$_2$O) $\lambda_{max}$ 335 nm 494 nm Cy5-(6-methyl-N-(6-amino)-caproamide-3-(triphospho-2-2deoxy-β-D-erythro-pentofuranosyl)pyrrolo[2,3-d]pyrimidin-2-one (10.1c)

This compound was prepared from (10.1a) in a similar manner as (8.1b) to afford (10.1c): UV (H$_2$O) $\lambda_{max}$ 355 nm, 648 nm

EXAMPLE 11

1-(2'-deoxy-5'-triphospho-β-D-ribofuranosyl)piperidino[2,3-d]pyrimidine-2(1H)-one (1.6), 6-methylamine-3-(5-triphospho-2-deoxy-β-D-erythro-pentofuranosyl)furano[2,3-d]pyrimidin-2-one) (3.3a) and 5-FAM-(6-methylamine-3-(5-triphospho-2-deoxy-β-D-erythro-pentofuranosyl)furano[2,3-d]pyrimidin-2-one) (3.3b), 6-methyl-N-(6-amino)-caproamide-3-(5-triphospho-2-deoxy-β-D-erythro-pentofuranosyl)furano[2,3-d]pyrimidin-2-one (4.3a) and 5-FAM-(6-methyl-N-(6-amino)-caproamide-3-(5-triphospho-2-deoxy-β-D-erythro-pentofuranosyl)furano[2,3-d]pyrimidin-2-one) (4.3b), 6-methylamine-3-(5-triphospho-2-deoxy-β-D-erythro-pentofuranosyl)pyrrolo[2,3-d]pyrimidin-2-one) (8.1), 6-methyl-N-(6-amino)-caproamide-3-(5-triphospho-2-deoxy-β-D-erythro-pentofuranosyl)pyrrolo[2,3-d]pyrimidin-2-one (10.1a), and the FAM and Cy5 of (10.1a, e.g. 10.1b and 10.1c) as substrates for terminal deoxynucleotidyl transferase. In order to test the ability of compounds (1.6), (3.3a), (3.3b), (4.3a), (4.3b), (8.1), (10.1a), (10.1b) and (10.1c) to be accepted by terminal deoxynucleotidyl transferase as a substrate, an oligonucleotide tailing reaction was performed.

A 15 mer primer (sequence: 5' TGC ATG TGC TGG AGA 3') and 8 to 32 base oligonucleotide markers were 5' end labelled with [γ$^{33}$P] ATP and T4 polynucleotide kinase. Reactions were boiled for 5 minutes after labelling to remove any PNK activity. Four picomoles of the labelled primer, 25 U terminal deoxynucleotidyl transferase and 32 μM dATP, dCTP, dGTP, dTTP or compounds (1.6), (3.3a), (3.3b), (4.3a), (4.3b), (8.1), (10.1a), (10.1b) and (10.1c) were incubated in 25 μl 100 mM cacodylate buffer pH7.2, 2 mM CoCl$_2$ and 0.2 mM 2-mercaptoethanol for 90 minutes at 37° C. The reactions were stopped by the addition of formamide stop solution and the reaction products run on a 19% polyacrylamide 7M urea gel with the labelled markers. Autoradiography using Biomax film was carried out on the dry gel.

The results showed that the natural nucleotides gave 3' tails in the region of 50 to 120 bases. The order of tail size being dTTP, dATP, dCTP then dGTP. Compound (1.6) gave 3' tails equivalent to those produced by dCTP at the same concentration. Compound (10.1a) gave a tail of ~7–8 bases. Compound (10.1b) gave tails in the 18–24 base range. Compound (10.1c) gave tails greater than 30 bases in length, which is surprising compared to the tails produced in the presence of fluor labelled natural dNTP's. Compound (8.1) produced a tail 2–3 bases in length. Compound (3.3a) gave a tail 2–3 bases in length. Compound (3.3b) produced a tail 2–3 bases in length. Compound (4.3a) gave a tail 7–9 bases in length. Compound (4.3b) gave a tail 9–14 bases in length.

This shows that the compounds of the invention are all substrates for terminal deoxynucleotidyl transferase and can therefore be incorporated into nucleic acids as a means of labelling or adding a new highly reactive functional group.

EXAMPLE 12

Primer Extension Assays to Study Incorporation of Nucleotides (10.1a), (10.1b) and (10.1c) by DNA Polymerases A primer extension assay was used to evaluate compounds (10.1a), (10.1b) and (10.1c) as substrates for exonuclease free Klenow fragment of DNA polymerase I (EFK). The assay used a $^{33}$P 5' end labelled 15 mer primer hybridised to a 24 mer template. The sequences of the primer and template are:

```
Primer      5' TGCATGTGCTGGAGA 3'

Template    3' ACGTACACGACCTCTGCCTTGCTA 5'
```

One picomole $^{33}$P labelled primer was hybridised to 2 picomoles of template in x2 Klenow buffer. To this was added either 20 μM dCTP or 20 μM (10.1a) or 20 μM (10.1b) or 20 μM (10.1c) or mixtures of dCTP and compound (10.1a) or compound (10.1b) or compound (10.1c) keeping the total nucleotide concentration fixed at 20 μM. One unit EFK and 2 mU inorganic pyrophosphatase were used per reaction. Primer alone, primer plus template plus enzyme controls were also carried out. The reactions were incubated at 37° C. for 3 minutes. Reactions were then stopped by the addition of formamide/EDTA stop solution. Reaction products were separated on a 19% polyacrylamide 7M urea gel and the product fragments sized by comparison with a $^{33}$P labelled 8 to 32 base oligonucleotide ladder after exposure to Kodak Biomax autoradiography film.

The autoradiogram showed that all three compounds were substrates for the polymerase being incorporated in place of dCTP. Compound (10.1a) was a surprisingly good substrate compared to the results obtained with similarly functionalised dCTP analogues like 5-allylaminocaproamido dCTP. This result shows that the analogues of this invention are useful in labelling DNA and also in introducing a highly reactive functionality into the DNA which would not normally be present.

EXAMPLE 13

Primer Extension Assays to Study Incorporation of Compounds (3.3a), (3.3b), (4.3a),(4.3b) and (8.1) by DNA Polymerases A primer extension assay was used to evaluate compounds (3.3a), (3.3b), (4.3a),(4.3b) and (8.1) as substrates for exonuclease free Klenow fragment of DNA polymerase I (EFK). The assay used a $^{33}$P 5' end labelled 15 mer primer hybridised to one of two 24 mer templates. The sequences of the primer and templates are:

```
Primer       5' TGCATGTGCTGGAGA 3'

Template 1   3' ACGTACACGACCTCTACCTTGCTA 5'

Template 2   3' ACGTACACGACCTCTGAACTAGTC 5'
```

One picomole $^{33}$P labelled primer was hybridised to 2 picomoles of template in x2 Klenow buffer. To this was added either 20 μM dCTP or 20 μM (3.3a) or 20 μM (3.3b) or 20 μM (4.3a) or 20 μM (4.3b) or 20 μM (8.1) or mixtures of dCTP and compound (3.3a) or (3.3b) or (4.3a) or (4.3b) or (8.1) keeping the total nucleotide concentration fixed at 20 μM. One unit EFK and 2 mU inorganic pyrophosphatase were used per reaction. Primer alone, primer plus template plus enzyme controls were also carried out. The reactions were incubated at 37° C. for 3 minutes. Reactions were then stopped by the addition of formamide/EDTA stop solution. Reaction products were separated on a 19% polyacrylamide 7M urea gel and the product fragments sized by comparison with a $^{33}$P labelled 8 to 32 base oligonucleotide ladder after exposure to Kodak Biomax autoradiography film.

The autoradiograms showed that compound (4.3b) was only incorporated in reactions using Template 2, thus indicating its preference for replacing dCTP. Compound (3.3b) was not a substrate for the polymerase using either of the Templates.

Compound (8.1) was a substrate for the polymerase being able to substitute for dCTP. Again this is very surprising as 5-allylaminocaproamide dCTP did not show any incorporation under similar assay conditions.

Compound (4.3a) was also a substrate for the polymerase again being able to replace dCTP. However, compound (3.3a) was not a substrate for the polymerase. This highlights the surprising nature of the results obtained with compounds (4.3a), (8.1) and (10.1a). In each case the analogue with the longer linker arm is the better substrate for the polymerase i.e. (10.1a) is a better substrate than (8.1), (4.3a) is a better substrate than (3.3a), which in fact is not a substrate for the polymerase under the conditions tested.

EXAMPLE 14
Primer Extension Assays to Study 1-(2'-deoxy-5'-triphospho-β-D-ribofuranosyl)piperidino[2,3-d]pyrimidine-2(1H)-one (1.6) Incorporation by DNA Polymerases A primer extension assay was used to evaluate compound (1.6) as a substrate for exonuclease free Klenow fragment of DNA polymerase I (EFK). The assay used a $^{33}$P 5' end labelled 15 mer primer hybridised to a 24 mer template. The sequences of the primer and template are:

```
Primer      5' TGCATGTGCTGGAGA 3'
Template    3' ACGTACACGACCTCTGAACTAGTC 5'
```

One picomole $^{33}$P labelled primer was hybridised to 2 picomoles of template in ×2 Klenow buffer. To this was added either 4 µM dNTPαS or 80 µM (1.6) or a mixture of 4 µM dNTPαS 80 µM (1.6). One unit EFK and 2 mU inorganic pyrophosphatase were used per reaction. Primer alone, primer plus template plus enzyme controls were also carried out. The reactions were incubated at 37° C. for 3 minutes. Reactions were then stopped by the addition of formamide I EDTA stop solution. Reaction products were separated on a 19% polyacrylamide 7M urea gel and the product fragments sized by comparison with a $^{33}$P labelled 8 to 32 base oligonucleotide ladder after exposure to Kodak Biomax autoradiography film.

This showed that (1.6) was a substrate for EFK and that it was efficiently incorporated in place of dCTP.

EXAMPLE 15
Incorporation of Compound (10.1a) into cDNA and PCR Products

1$^{st}$ Strand cDNA Synthesis

Incorporation of compound (10.1a) into 1$^{st}$ strand cDNA was carried out using a balance of dCTP such that the total concentration of (10.1a) and dCTP was equivalent to each of the other three dNTP concentrations.

(10.1a) was used at three different percentages 1) 50% (10.1a)
2) 75% (10.1a)
3) 100% (10.1a)

| Nucleotide Solutions | | | |
|---|---|---|---|
| (10.1a) level | 50% | 75% | 100% |
| 10 mM dATP | 1 µl | 1 µl | 1 µl |
| 10 mM dGTP | 1 µl | 1 µl | 1 µl |
| 10 mM dTTP | 1 µl | 1 µl | 1 µl |
| 5 mM dCTP | 1 µl | 0.5 µl | 0 µl |
| 5 mM (10.1a) | 1 µl | 0.5 µl | 2 µl |

These reactions were compared with reactions including Cy5 labelled dCTP. All reactions were monitored by carrying out the reaction in duplicate and monitoring one of the duplicates with a spike of $^{33}$P-dATP.

Reaction Matrix

Sample 1. 50% (10.1a)
2. 50% (10.1a)+$^{33}$P-dATP
3. 75% (10.1a)
4. 75% (10.1a)+$^{33}$P-dATP
5. 100% (10.1a)
6. 100% (10.1a)+$^{33}$P-dATP Cy5 dCTP Cy5 dCTP+$^{33}$P-dATP 1$^{st}$ Strand cDNA Synthesis To a reaction tube add:

1 µg mRNA

1 µg anchored dT$_{(25)}$ primer

10 µl water

Heat at 70° C. for 5 minutes

Incubate at room temp. for 10 minutes

Transfer tube to ice and add

4 µl buffer

4 µl NaPPi

1 µl HPRI

1 µl dNTP mix (50%, 75% or 100% (10.1a)) or Cy5 dCTP

1 µl $^{33}$P-dATP-active samples only

1 µl AMV reverse transcriptase 20 U/µl

Incubate at 42° C. for 2½ hours

Store on ice

Alkaline Hydrolysis

Heat reactions at 94° C. for 3 minutes

Add 1 µl of 5M NaOH

Incubate at 37° C. for 10 minutes

Add 1 µl of 5M HCl

Add 5 µl of 1M Tris.HCl, pH 6.8

Mix and centrifuge briefly.

The cDNA reactions were monitored by TLC as follows

1 μl of sample was spotted onto PEI cellulose TLC plates and run in 1.25M Potassium phosphate buffer

| TLC results | |
|---|---|
| (10.1a) | $^{33}$P-dATP Incorporation |
| 50% | 23.2% |
| 75% | 16.5% |
| 100% | 11.5% |
| Standard cDNA | 15.9% |

Samples were then purified by Qiagen column and eluted in 50 μl of water. The active cDNA products were analysed on a 6% polyacrylamide gel 8 μl of sample+3 μl of loading dye Run at 35 mV for 1½ hours The gel was then covered in Saran wrap and exposed to phosphorscreen for 1 hour. Phosphorscreen analysis was carried out on the Molecular Dynamics Storm 860 instrument.

Results

6% polyacrylamide gel analysis showed that cDNA products had been made in all reactions.

PCR Reactions

Incorporation of (10.1a) into arabidopsis DNA by PCR was carried out as follows:

The (10.1a) was used in the PCR at various percentages with a balance of dCTP such that the total concentration of (10.1a) and dCTP was equivalent to each of the other three base dNTP's. The percentages of (10.1a) used were:

%(10.1a)
0%
5%
10%
20%
30%
40%
50%
100%

Compound (10.1a) PCR conditions
To each reaction tube was added

| | |
|---|---|
| *Arabidopsis thaliana* template DNA (100 pg/μl) | 5 μl |
| 10X PCR reaction buffer | 5 μl |
| T7 forward primer (5 μM) | 5 μl |
| T3 reverse primer (5 μM) | 5 μl |
| dATP (4 mM) | 2.5 μl |
| X% (10.1a) (4 mM) | 2.5 μl |
| dGTP (4 mM) | 2.5 μl |
| dTTP (4 mM) | 2.5 μl |
| *Thermus aquaticus* DNA polymerase (5 units/μl) | 0.5 μl |
| water | 19.5 μl |
| Total | 50 μl |

The reaction mix was covered with two to three drops of mineral.

The reaction tubes were placed in the PCR thermocycling block.

PCR Thermocycling:—Carried Out in a Perkin Elmer DNA Thermal Cycler 480

| 35 cycles of | |
|---|---|
| 94° C. | 45 seconds |
| 45° C. | 45 seconds |
| 72° C. | 2 minutes |
| Followed by | |
| 72° C. | 8 minutes |
| 4° C. | soak |

After PCR, the samples were purified by Qiagen column and analysed by 1% agarose gel.

10 μl sample+1 μl Vistra green

Run at 150V for 1½ hours

Results

Agarose gel analysis showed that all levels of (10.1a) resulted in the formation of PCR product EXCEPT for the 100% (10.1a) level.

Attachment of Cy5 NHS-Ester to (10.1a) Incorporated into cDNA and PCR Product

Cy5 NHS-Ester was coupled to (10.1a) bases incorporated into DNA by the above methods as follows:

Cy5 NHS-Ester (Amersham Pharmacia Biotech)

Q15108 Lot: 973181

1 vial dissolved in 1 ml of dry DMF

Labelling reaction

20 μl DNA

5 μl Cy5 NHS-Ester

25 μl sodium bicarbonate buffer, pH 9.3

50 μl Total volume

| Labelling Matrix | | |
|---|---|---|
| Tube | % (10.1a) | Inc. Method |
| 1 + 2 | 0 | PCR |
| 3 + 4 | 5 | PCR |
| 5 + 6 | 10 | PCR |
| 7 + 8 | 20 | PCR |
| 9 + 10 | 30 | PCR |
| 11 + 12 | 40 | PCR |
| 13 + 14 | 50 | PCR |
| 15 + 16 | 75 | cDNA |
| 17 + 18 | 100 | cDNA |
| 19 + 20 | M13- standard DNA to check for non-specific labelling | |

The dye was allowed to react with the (10.1a) groups in the DNA for 16 hours (overnight)

The following day, 2 μl of one of each duplicate was analysed on silica gel TLC.

TLC system

Silica gel—normal phase, 740238909 (Merck)

Solvent—60% IPA (iso propyl alcohol)
20% NH$_4$OH
20% Water

The samples were spotted and run for 1 hour. The TLC sheet was then dried and analysed on the Molecular Dynamics Storm 860 instrument.

Cy5 NHS-Ester Labelling Results

The scan showed evidence of Cy5 labelling in tubes 1–18, but not tubes 19–20, indicating that the NHS-Ester has coupled with the (10.1a) groups incorporated into the DNA. Increasing Cy5 labelling was seen with increasing percentage of compound (10.1a) in the reaction. This clearly shows the ability of this analogue to introduce functionality into the DNA. This functionality could be used for labelling as above or for attachment to a solid support.

What is claimed is:

1. A compound having the structure

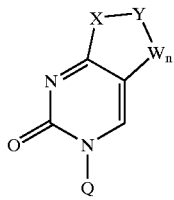

where X=O or NH or S

Y=N or CHR$^6$ or CR$^6$ or CO

W=N or NR$^6$ or CHR$^6$ or CR$^6$ or S or CO n=2 each R$^6$ is independently H or alkyl or alkenyl or alkoxy or aryl or a reporter moiety, if Y or W=N or CR$^6$, then a double bond is present between the Y and W or between the W and W, and Q is selected from the group consisting of H, a sugar, a sugar analogue, a nucleic acid backbone, and backbone analogue provided that (i) when X is NH and W is CHR$^6$ or CR$^6$, and Y is CO, then at least one R$^6$ is a reporter moiety, (ii) when W is S, then W$_n$ is —CHR$^6$—S— or =CR$^6$—S—, (iii) when X is NH and Y is CHR$^6$ or CR$^6$, then at least one R$^6$ is a reporter moiety that is selected from the group consisting of a reactive group, signal moiety, and solid surface joined to the remainder of the molecule by a linker of at least 3 chain atoms, and (iv) when X is O and Y is CHR$^6$ and W is CHR$^6$ or S, then at least one R$^6$ is a reporter moiety.

2. The compound of claim 1 wherein the compound is (a) a nucleoside or nucleoside analogue wherein Q is

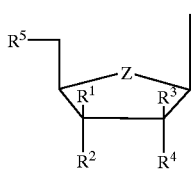

where Z is O

R$^1$, R$^2$, R$^3$ and R$^4$ are the same or different and each is H or OH

R$^5$ is mono-, di-, or tri-phosphate, or one of R$^2$ and R$^5$ is a phosphoramidite or other group for incorporation in a polynucleotide chain; or (b) a polynucleotide wherein Q is a nucleic acid backbone selected from the group consisting of sugar-phosphate repeats, modified sugar-phosphate repeats (LNA), or a backbone analogue such as peptide or polyamide nucleic acid (PNA).

3. A compound of claim 1 wherein the structure is selected from the group consisting of

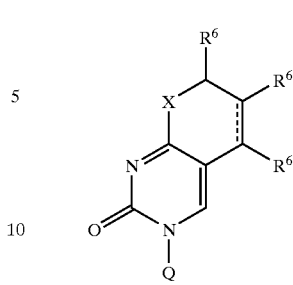

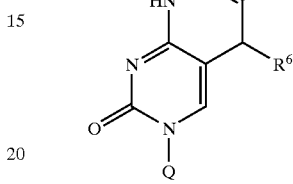

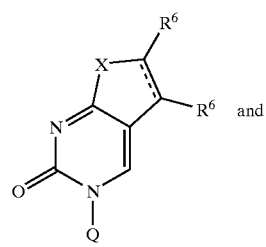 and

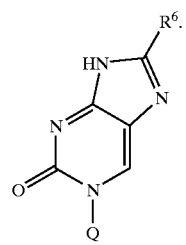

4. The compound of claim 3, wherein a reporter moiety is present.

5. The compound of claim 4, wherein the reporter moiety is a signal moiety.

6. The compound of claim 4, wherein the reporter moiety is a reactive group or signal moiety or solid surface joined to the remainder of the molecule by a linker of at least 3 chain atoms.

7. The compound of claim 3, wherein R$^5$ is triphosphate.

8. The compound of claim 3, wherein one of R$^2$ and R$^5$ is selected from phosphoramidite and H-phosphonate.

9. A polynucleotide comprising at least one residue of the compound of claim 1.

10. The polynucleotide of claim 9, wherein the polynucleotide is DNA or RNA.

11. A chain extension method which comprises reacting a polynucleotide with a nucleoside triphosphate analogue of claim 1 in the presence of a polymerase or a terminal deoxynucleotidyl transferase enzyme.

12. A method of detecting the polynucleotide of claim 9, which method comprises using for detection an antibody which binds to a base component selected from the group consisting of structure (1), structure (2), structure (3), and structure (4).

13. A method of making cDNA which comprises incubating an RNA template with a monomer mixture including a nucleotide analogue as claimed in claim 1 in the presence of a reverse transcriptase.

14. A method of amplifying a polynucleotide by PCR which method comprises using a monomer mixture including a nucleotide analogue as claimed in claim 1.

15. A method of reducing compression artefacts in nucleic acid sequencing, comprising (a) incorporating at least one nucleoside analogue of claim 1 into polynucleotides using a polymerase; and
(b) separating polynucleotides created by the polymerase by electrophoresis, wherein incorporation of the nucleoside analogue into one or more polynucleotides reduces detection of compression artefacts.

16. A method of detecting a residue of the compound of claim 1, the method comprising analyzing by mass spectrometry.

* * * * *

UNITED STATES PATENT AND TRADEMARK OFFICE
CERTIFICATE OF CORRECTION

PATENT NO. : 6,605,611 B2 Page 1 of 1
DATED : August 12, 2003
INVENTOR(S) : Adrian Christopher Simmonds et al.

It is certified that error appears in the above-identified patent and that said Letters Patent is hereby corrected as shown below:

<u>Title page,</u>
Item [73], Assignee, should read -- AMERSHAM PLC --

Signed and Sealed this

Twenty-seventh Day of January, 2004

JON W. DUDAS
*Acting Director of the United States Patent and Trademark Office*